United States Patent
Yen et al.

(10) Patent No.: US 10,388,887 B2
(45) Date of Patent: Aug. 20, 2019

(54) DELAYED FLUORESCENCE COMPOUND FOR ORGANIC EL DEVICE AND USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

( * ) Notice: Subject to any disclaimer, the term of this patent is extended or adjusted under 35 U.S.C. 154(b) by 287 days.

(21) Appl. No.: 15/368,682

(22) Filed: Dec. 5, 2016

(65) Prior Publication Data
US 2018/0159049 A1 Jun. 7, 2018

(51) Int. Cl.
| H01L 51/00 | (2006.01) |
| C09K 11/06 | (2006.01) |
| C09K 11/02 | (2006.01) |
| C07D 471/04 | (2006.01) |
| C07D 519/00 | (2006.01) |
| H01L 51/50 | (2006.01) |

(52) U.S. Cl.
CPC ........ *H01L 51/0072* (2013.01); *C07D 471/04* (2013.01); *C07D 519/00* (2013.01); *C09K 11/02* (2013.01); *C09K 11/06* (2013.01); *H01L 51/0071* (2013.01); *H01L 51/5004* (2013.01); *C09K 2211/1007* (2013.01); *C09K 2211/1044* (2013.01); *H01L 51/5012* (2013.01); *H01L 51/5016* (2013.01); *H01L 51/5072* (2013.01); *H01L 51/5096* (2013.01); *H01L 2251/5361* (2013.01); *H01L 2251/5376* (2013.01)

(58) Field of Classification Search
CPC ............... C07D 471/04; C07D 519/00; C09K 2211/1044; C09K 2211/1059
See application file for complete search history.

(56) References Cited

U.S. PATENT DOCUMENTS

| 7,601,435 B2 | 10/2009 | Shitagaki et al. |
| 2010/0237339 A1 | 9/2010 | Nomura et al. |
| 2015/0166886 A1 | 6/2015 | Endo et al. |

FOREIGN PATENT DOCUMENTS

WO 2015099486 A1 2/2015

OTHER PUBLICATIONS

Liu B. et al, Chem. Eur. J. Molecular Engineering of Pyrido[3.4-b]pyrazilne-based Donor-Acceptor-pi-acceptor Organic Sensitizers: Effects of Auxiliary Acceptor in Cobalt- and Iodine-based Electrolytes, Nov. 9, 2015, 21, 18654-61. (Year: 2015).*

* cited by examiner

*Primary Examiner* — Jennifer A Chriss
*Assistant Examiner* — Sean M DeGuire

(57) ABSTRACT

The present invention discloses a delayed fluorescence compound and the organic EL device employing the delayed fluorescence compound as light emitting host of emitting lay and/or an electron transporting layer, and/or a hole blocking layer, and/or a delayed fluorescence material of emitting layer for organic EL device in the present invention display good performance.

18 Claims, 5 Drawing Sheets

| 14 | — metal electrode |
| 13 | — electron injection layer |
| 12 | — electron transport layer |
| 11 | — hole blocking layer |
| 10 | — emitting layer |
| 9 | — electron blocking layer |
| 8 | — hole transport layer |
| 7 | — hole injection layer |
| 6 | — transparent electrode |

DELAYED FLUORESCENCE COMPOUND FOR ORGANIC EL DEVICE AND USING THE SAME

FIELD OF INVENTION

The present invention relates to a compound and organic electroluminescence (herein referred to as organic EL) device using the compound. More specifically, the present invention relates to a delayed fluorescence compound having general formula (1), and an organic EL device using the delayed fluorescence compound display excellent performance.

BACKGROUND OF THE INVENTION AND PRIOR ART

Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

A new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC) by using a material having a small energy gap between the singlet level and the triplet level. However, further improvement in luminous efficiency of the organic EL device in a high current density region is still desired.

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting panel the material used for the phosphorescent host for emitting layer are still unsatisfactory in half-lifetime, efficiency and driving voltage for industrial practice use. Besides, in order to display excellent performance of organic EL devices, the phosphorescent light emitting host material need to collocate with other organic thin film layer such as hole blocking layer and electron transporting layer to get lower power consumption, longer half-life time and higher efficiency. Therefore, there is a demand for designing and developing novel material for organic EL devices.

In the present invention, for the purpose to prolong the half-life time, higher efficiency and display excellent performance for dipolar materials of delayed fluorescence compound for organic EL device, we employ 2,3-diphenylpyrido [3,4-b]pyrazine skeleton act as acceptor and utilize 5 and/or 8 positions of the skeleton link to donor characteristic of carbazole group, bicarbazole group, dihydroindolocarbazole group, dihydroindenocarbazole group, phenothiazine group, phenoxazine group, dihydroacridine group, dihydrophenazine group and dihydrophenazine group to finish the delayed fluorescence compound as general formula (1). Prior art U.S. Pat. No. 7,601,435, US20100239339A1, WO2015099486, WO2016013875 disclosed quinoxaline related compounds, and introduce substituent in 6 and 7 position of quinoxaline core. P. Brogdon, et al., reported quinoxaline-based dyes for the highest efficiency dye-sensitized solar cell (DSC) devices. (SYNMET 15280 No. of Pages 10). There are no prior arts demonstrate an 2,3-diphenylpyrido [3,4-b]pyrazine skeleton as acceptor of delayed fluorescence compound for organic EL device.

SUMMARY OF THE INVENTION

According to the reasons described above, the present invention has the objective of resolving such problems of the prior art and offering a light emitting device which is excellent in its thermal stability, high luminance efficiency and long half-life time. The present invention disclose a delayed fluorescence compound having general formula (1), used as delayed fluorescence material of emitting layer and/or phosphorescent light emitting host of emitting layer, and/or an electron transporting layer, and/or a hole blocking layer having good charge carrier mobility and excellent operational durability can lower driving voltage and power consumption, increasing efficiency and half-life time of organic EL device.

The present invention has the economic advantages for industrial practice. Accordingly, the present invention discloses the delayed fluorescence compound which can be used for organic EL device is disclosed. The mentioned the delayed fluorescence compound is represented by the following formula (1):

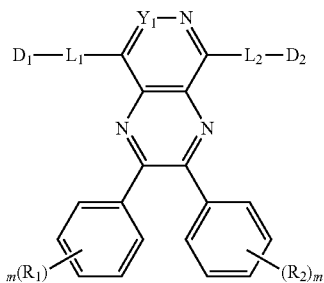

formula(1)

wherein $D_1$ and $D_2$ are independently selected from the group consisting of formula (2) to formula (6):

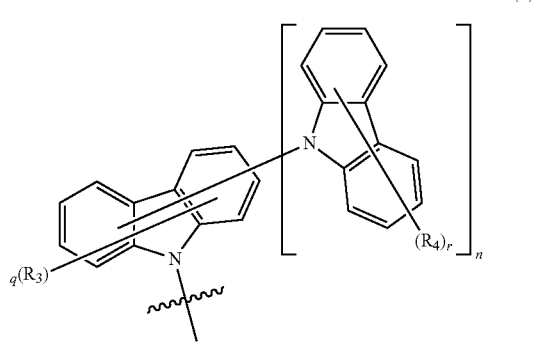

formula(2)

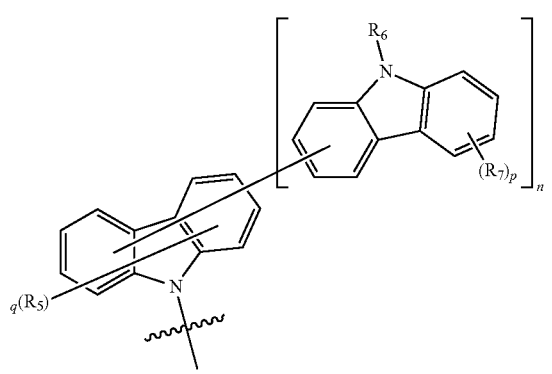

formula(3)

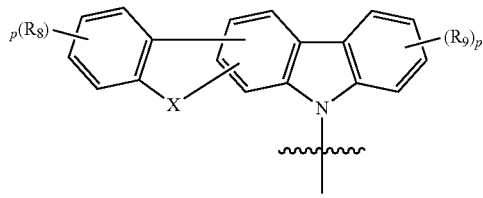

formula(4)

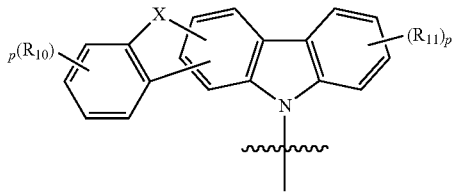

formula(5)

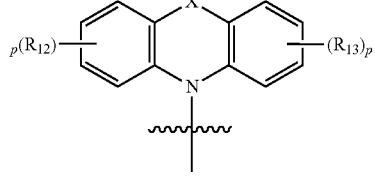

formula(6)

L represents a single bond, a substituted or unsubstituted arylene group having 6 to 30 ring carbon atoms, or a substituted or unsubstituted heterarylene group having 3 to 30 ring carbon atoms, m represent an integer of 0 to 5, n represents an integer of 0 to 2, p represents an integer of 0 to 4, q represents an integer of 0 to 7, r represents an integer of 0 to 8, X is a divalent bridge selected from the atom or group consisting from O, S, $C(R_{14})(R_{15})$, $NR_{16}$ and $Si(R_{17})(R_{18})$, $Y_1$ represents a nitrogen atom or $C(R_s)$, and each $R_s$ represents a hydrogen, a phenyl, a substituted or unsubstituted alkyl group having 1 to 30 carbon atoms, a substituted or unsubstituted aryl group having 6 to 30 carbon atoms; $R_1$ and $R_2$ are independently selected from the group consisting of a hydrogen atom, a halide, a nitro, a pyridine, a pyrazine, a pyrimidine, a triazine, a substituted or unsubstituted alkyl group having 1 to 30 carbon atoms and a substituted or unsubstituted aryl group having 6 to 30 carbon atoms, $R_3$ to $R_{18}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

DESCRIPTION OF THE PREFERRED EMBODIMENTS

Figure 1:
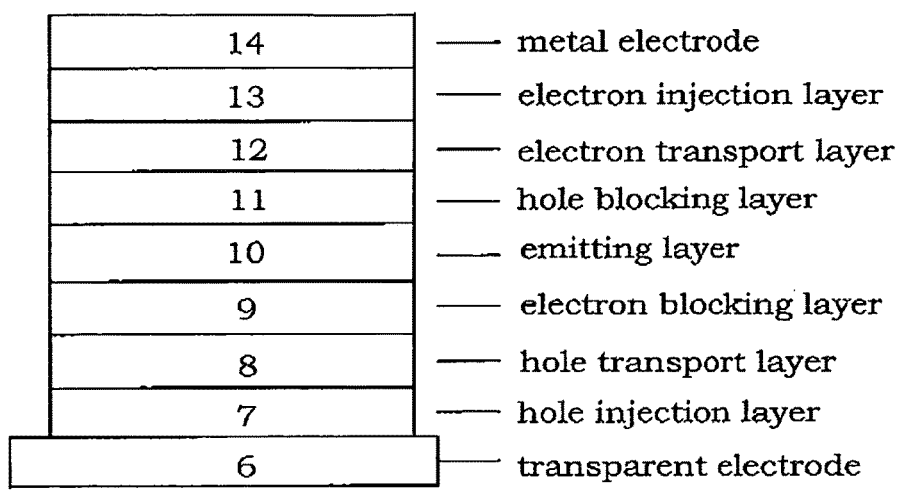
FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is emitting layer which is deposited onto 9, 11 is hole blocking layer which is deposited onto 10, 12 is electron transport layer which is deposited on to 11, and 13 is electron injection layer which is deposited on to 12.

What probed into the invention is the delayed fluorescence compound for organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the delayed fluorescence compound which can be used as a thermally activated delayed fluorescence (TADF) material of emitting layer for organic EL device are disclosed. The mentioned the delayed fluorescence compound represented by the following formula (1):

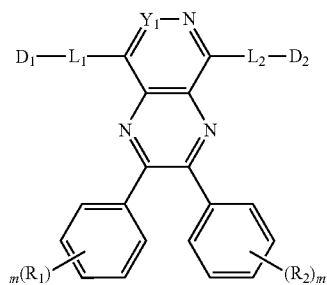

formula(1)

wherein $D_1$ and $D_2$ are independently selected from the group consisting of formula (2) to formula (6):

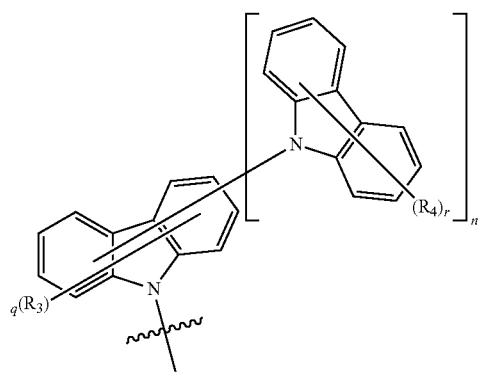

formula(2)

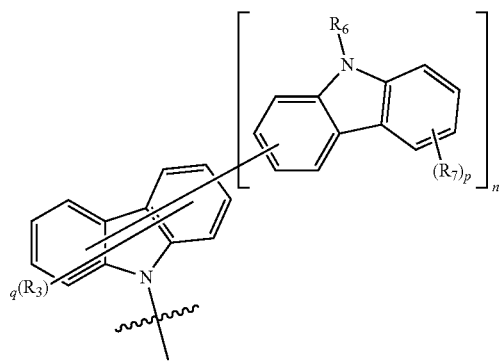

formula(3)

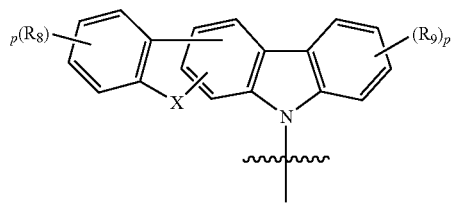

formula(4)

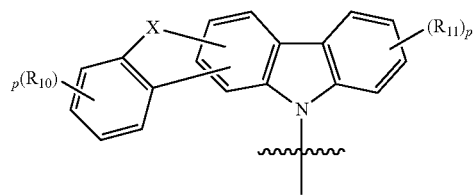

formula(5)

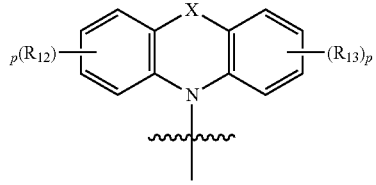

formula(6)

L represents a single bond, a substituted or unsubstituted arylene group having 6 to 30 ring carbon atoms, or a substituted or unsubstituted heterylene group having 3 to 30 ring carbon atoms, m represent an integer of 0 to 5, n represents an integer of 0 to 2, p represents an integer of 0 to 4, q represents an integer of 0 to 7, r represents an integer of 0 to 8, X is a divalent bridge selected from the atom or group consisting from O, S, $C(R_{14})(R_{15})$, $NR_{16}$ and $Si(R_{17})(R_{18})$, $Y_1$ represents a nitrogen atom or $C(R_s)$, and each $R_s$ represents a hydrogen, a phenyl, substituted or unsubstituted alkyl group having 1 to 30 carbon atoms, a substituted or unsubstituted aryl group having 6 to 30 carbon atoms; $R_1$ and $R_2$ are independently selected from the group consisting of a hydrogen atom, a halide, a nitro, a pyridine, a pyrazine, a pyrimidine, a triazine, a substituted or unsubstituted alkyl group having 1 to 30 carbon atoms and a substituted or unsubstituted aryl group having 6 to 30 carbon atoms, $R_3$ to $R_{18}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

According to the above-mentioned the delayed fluorescence compound formula (1), wherein $L_1$ and $L_2$ are represented by the following formula (7):

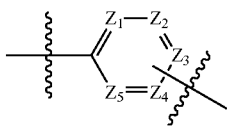

formula(7)

wherein $Z_1$ to $Z_5$ independently represent a nitrogen atom or $C(R_s)$, and each $R_s$ represents a hydrogen, a phenyl, a substituted or unsubstituted alkyl group having 1 to 30 carbon atoms, a substituted or unsubstituted aryl group having 6 to 30 carbon atoms.

In this embodiment, some delayed fluorescence compounds are shown below:

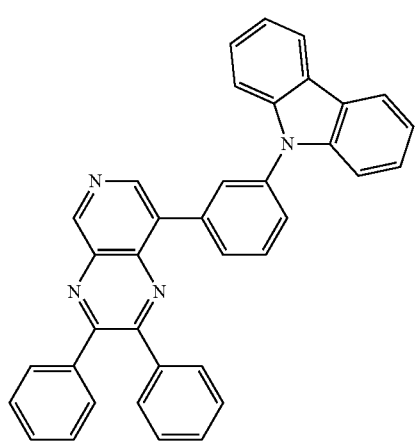

C1

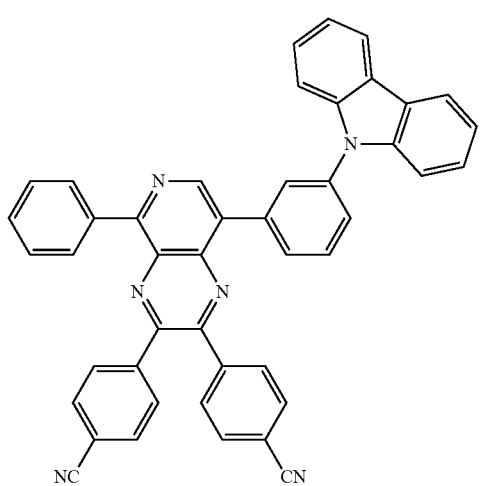

C2

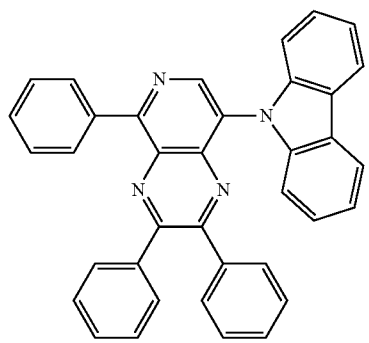

C3

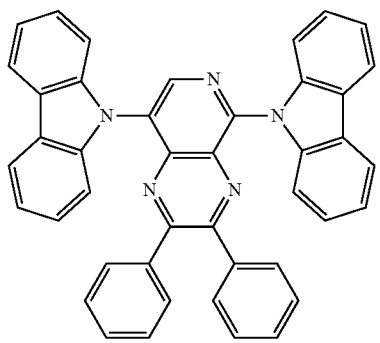

C4

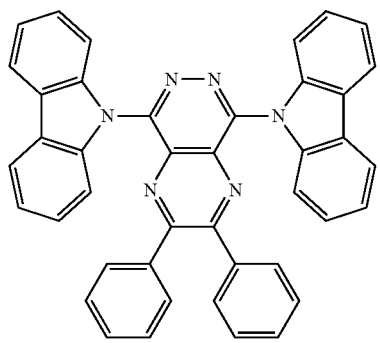

C5

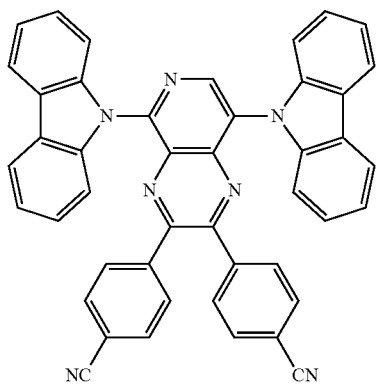

C6

-continued
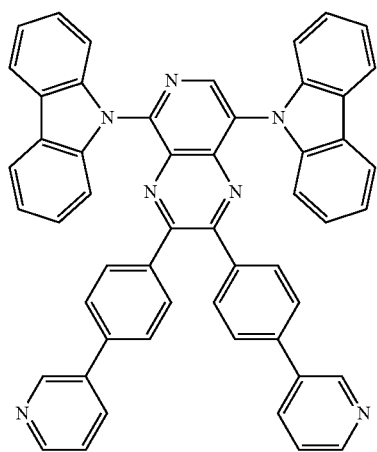
C7
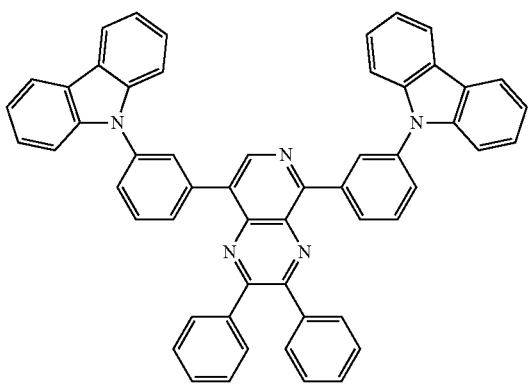
C8
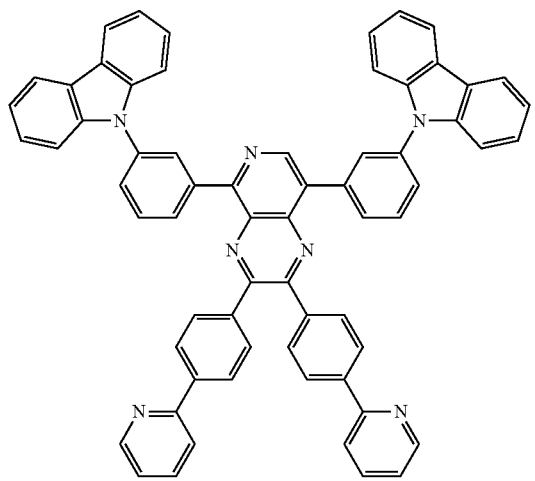
C9
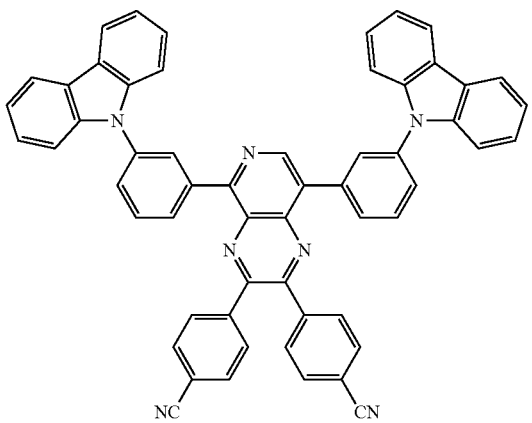
C10
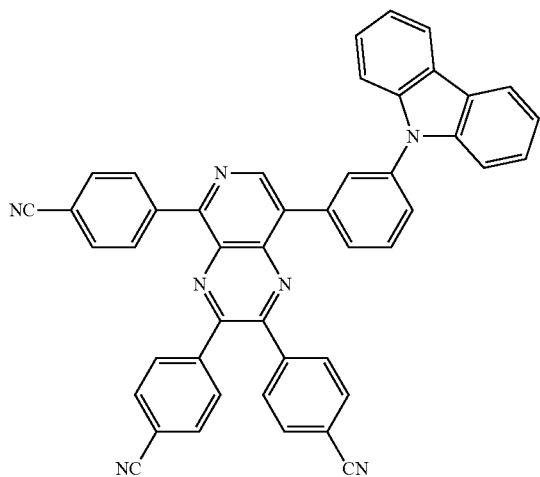
C11
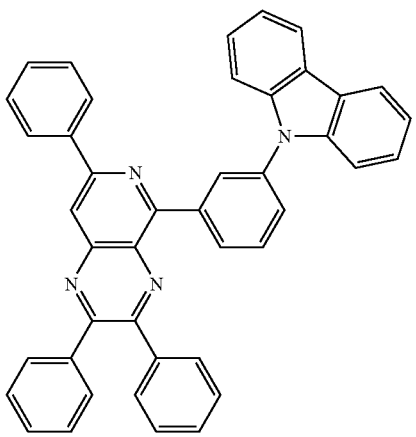
C12

C13
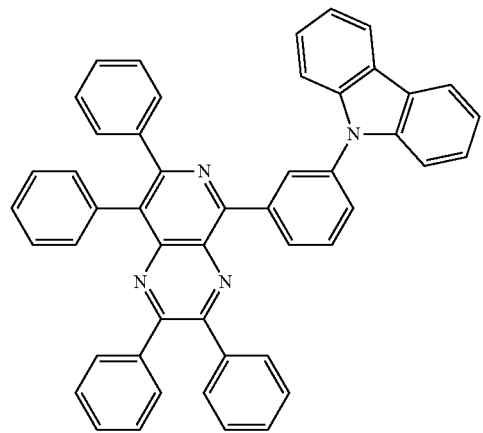
C14
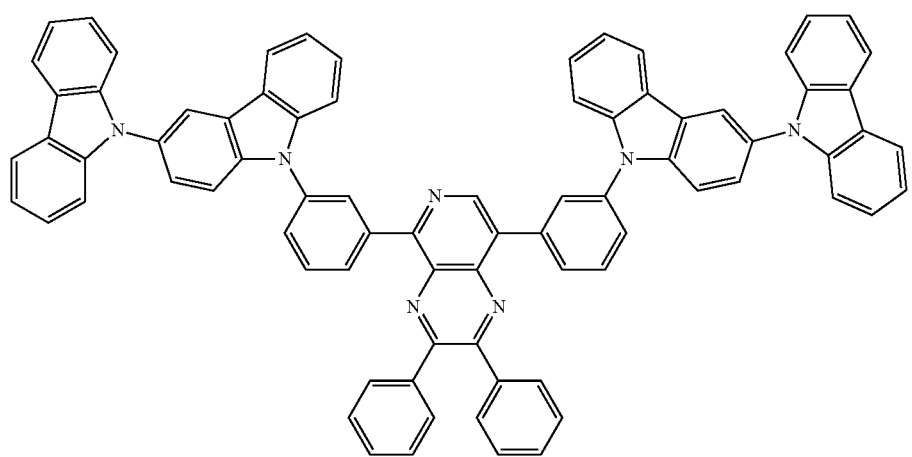
C15
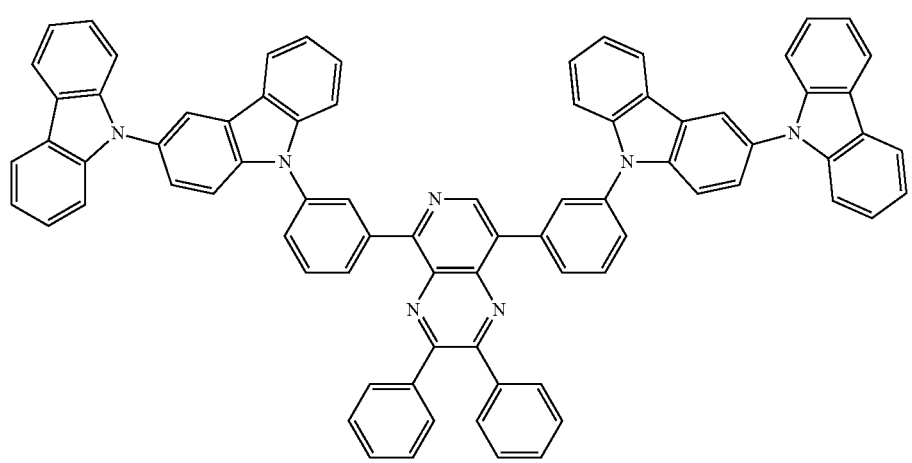

-continued
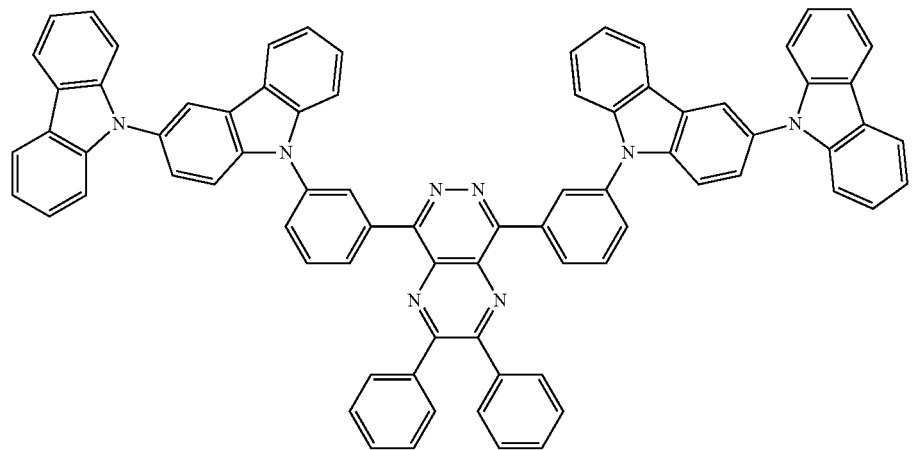
C16
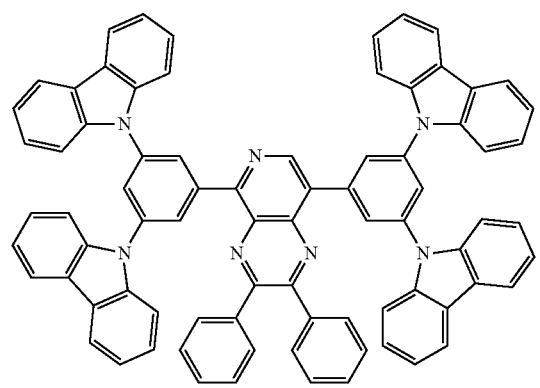
C17
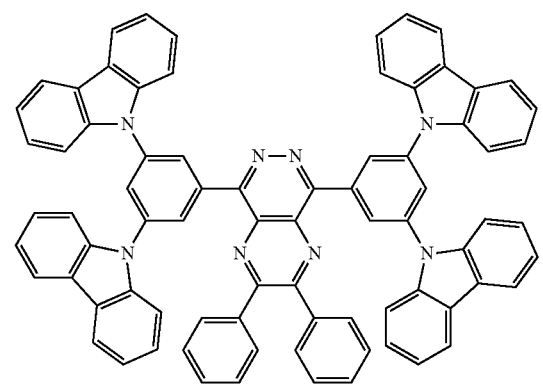
C18
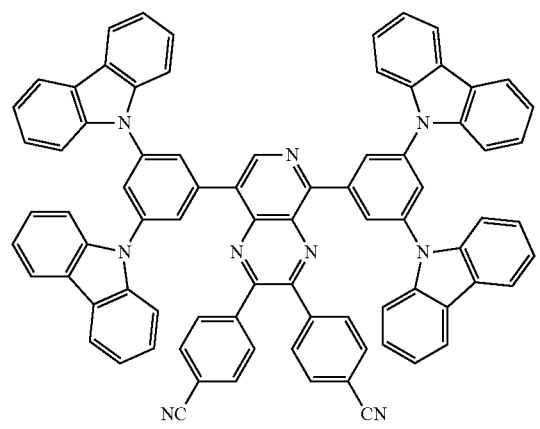
C19
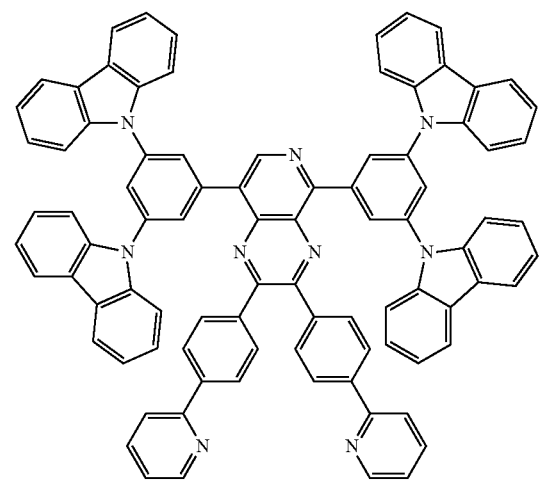
C20

-continued
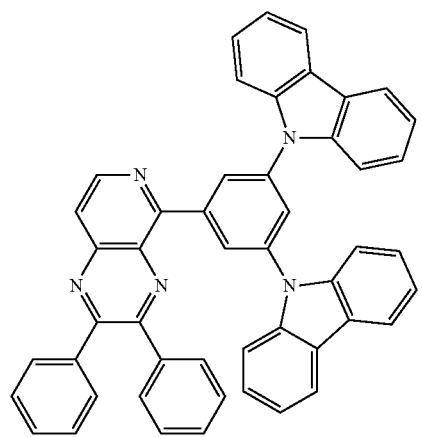
C21
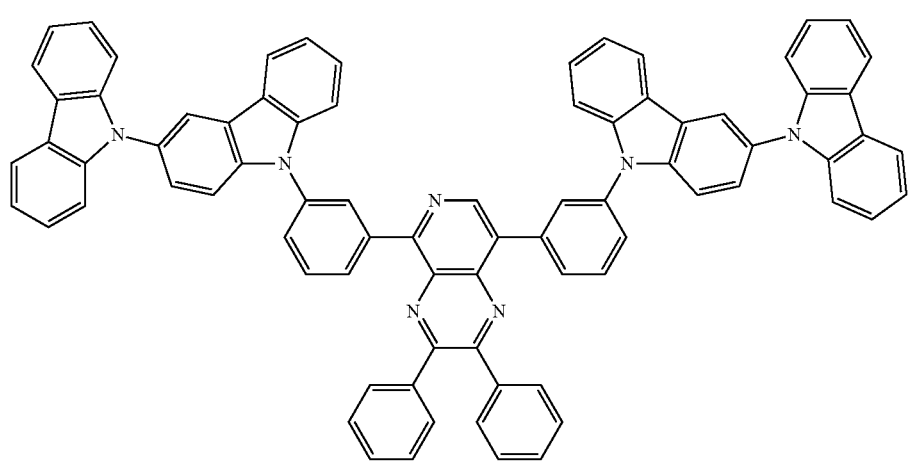
C22
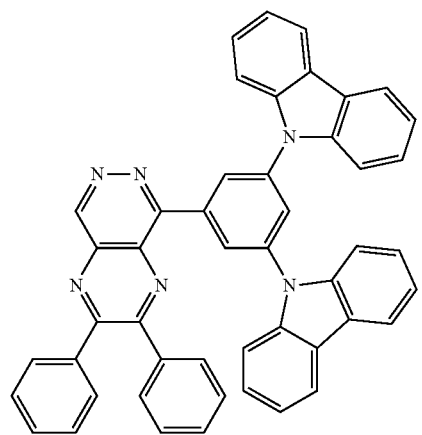
C23
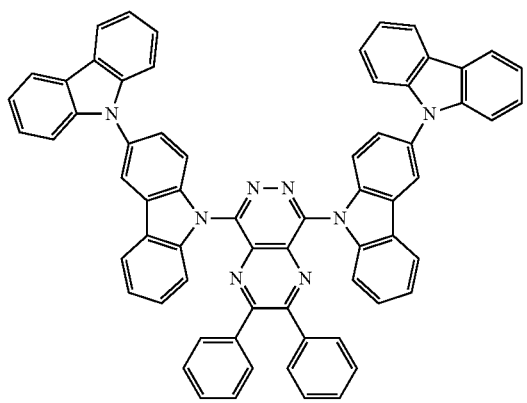
C24

-continued
C25 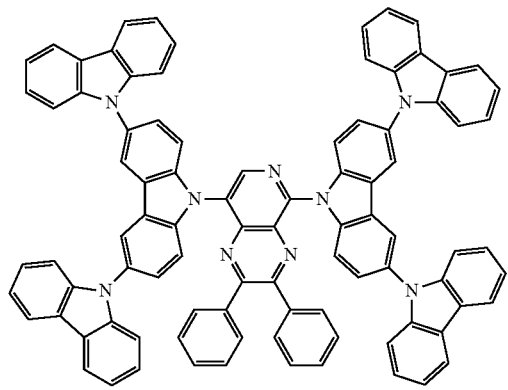
C26 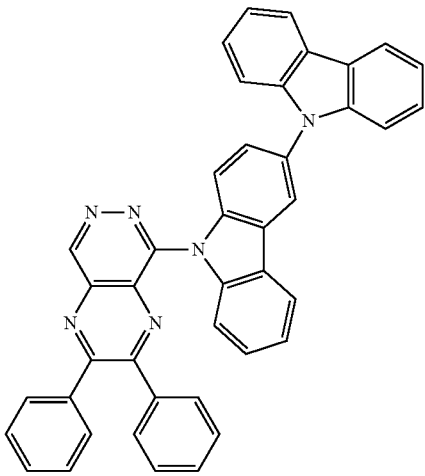
C27 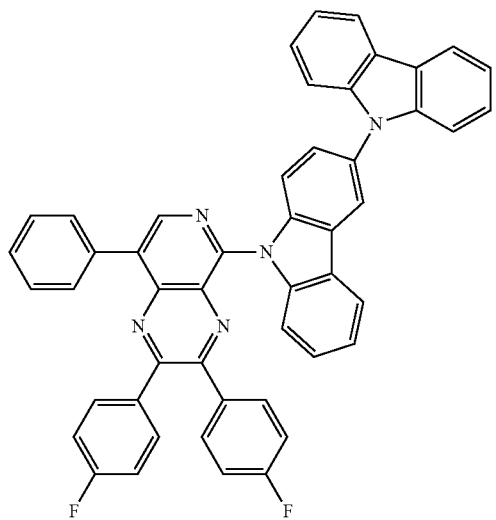
C28 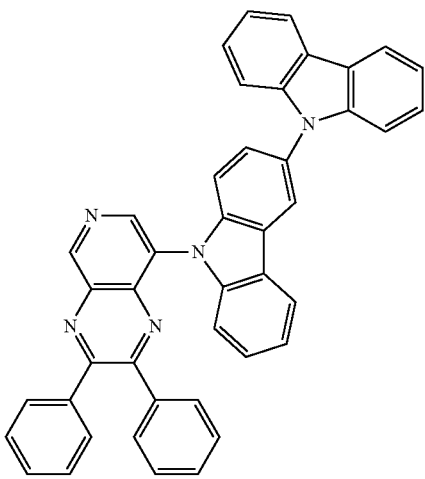
C29 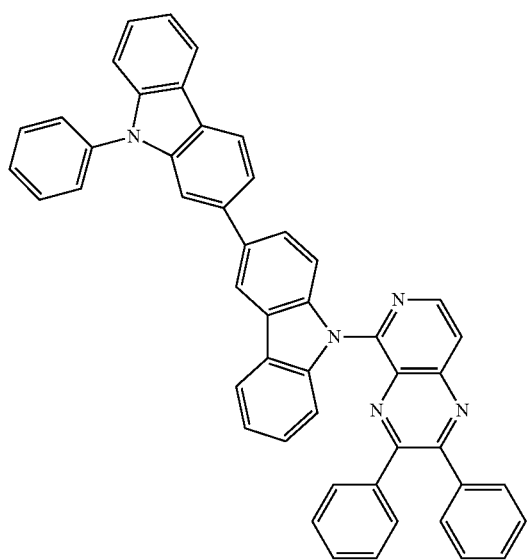
C30 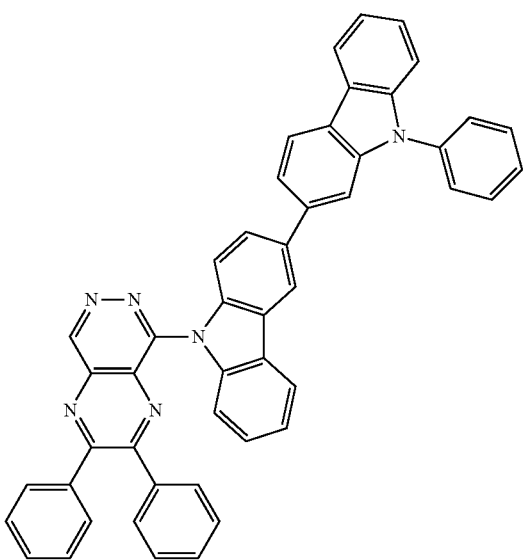

-continued
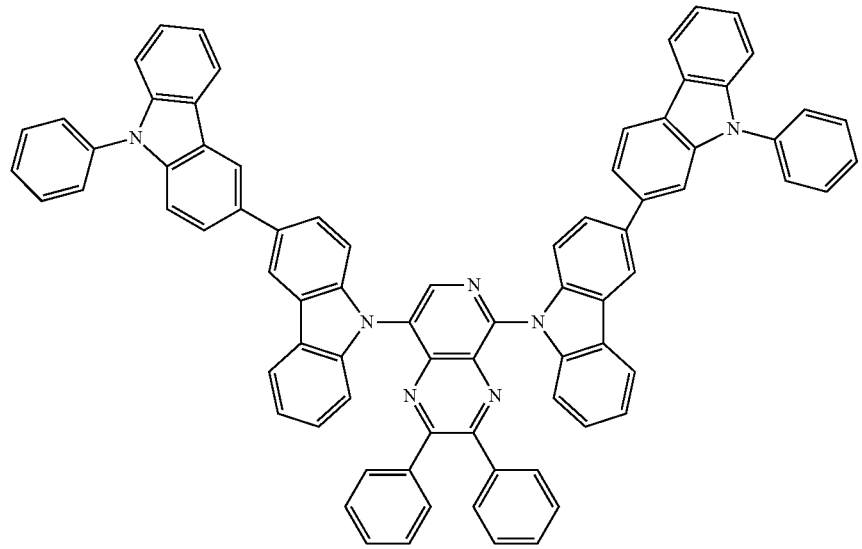
C31
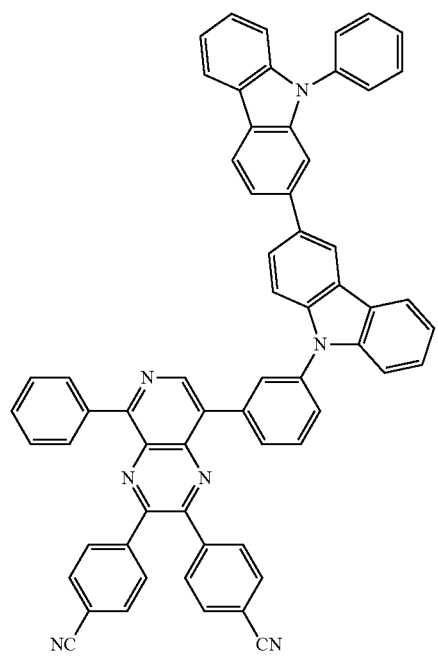
C32
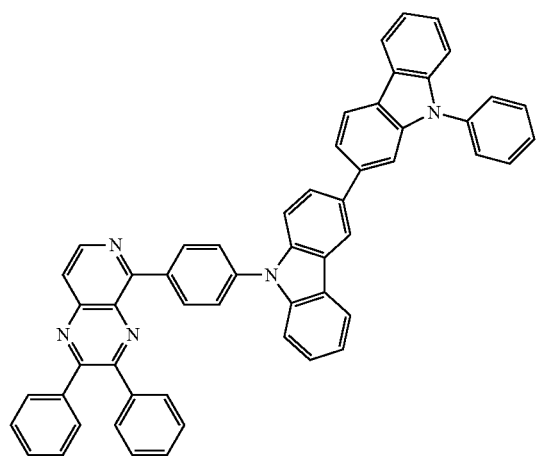
C33

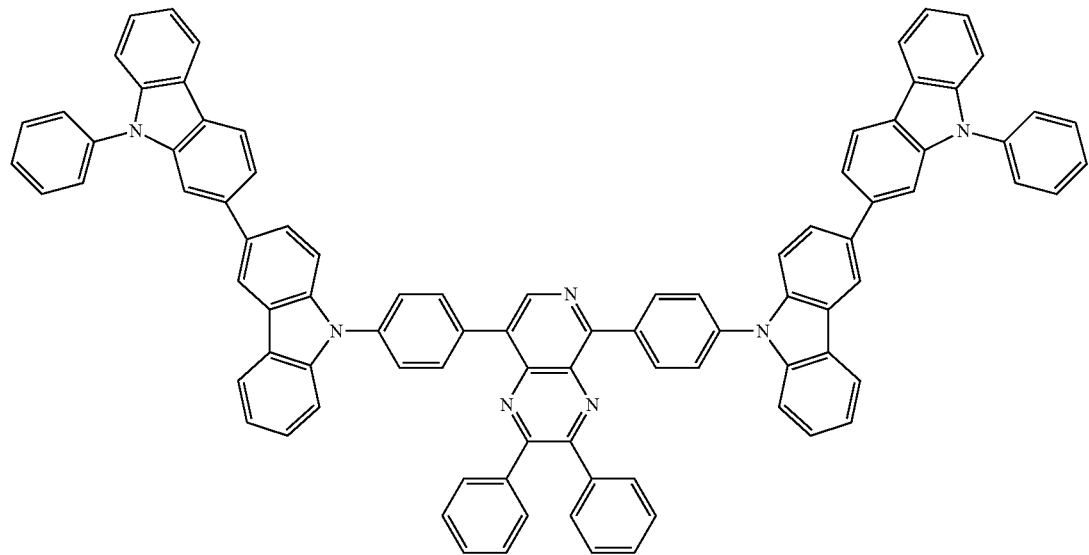
C34
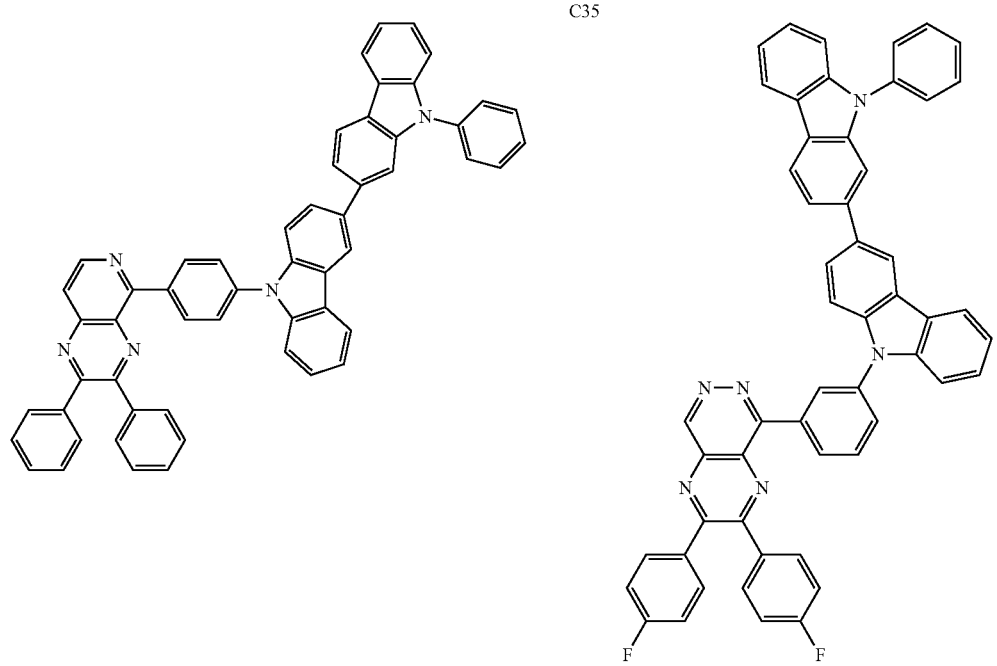
C35
C36

-continued
C37
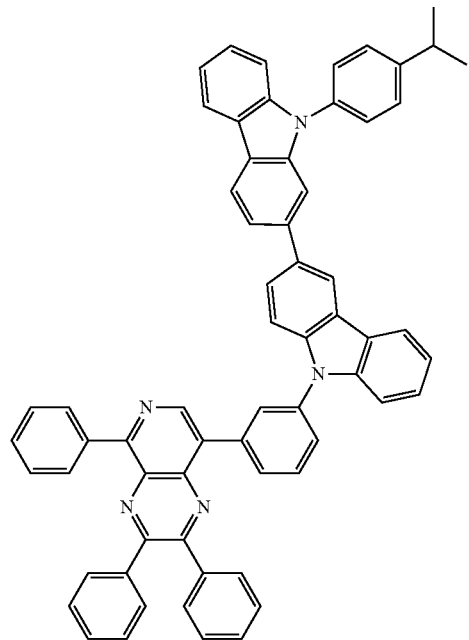
C38
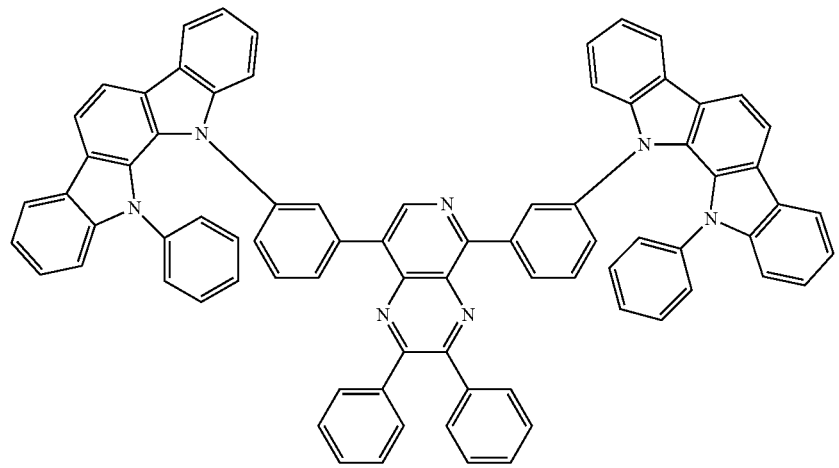
C39
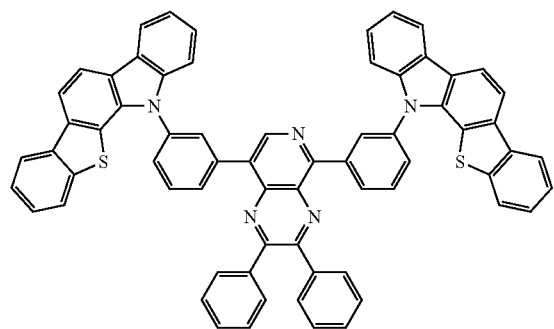
C40
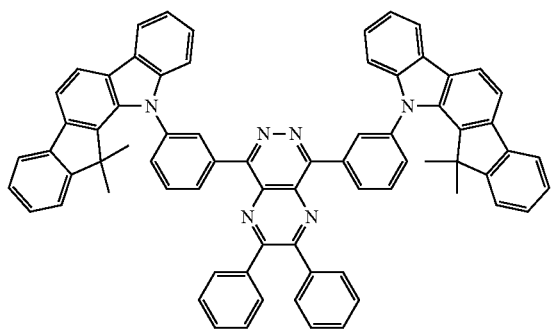

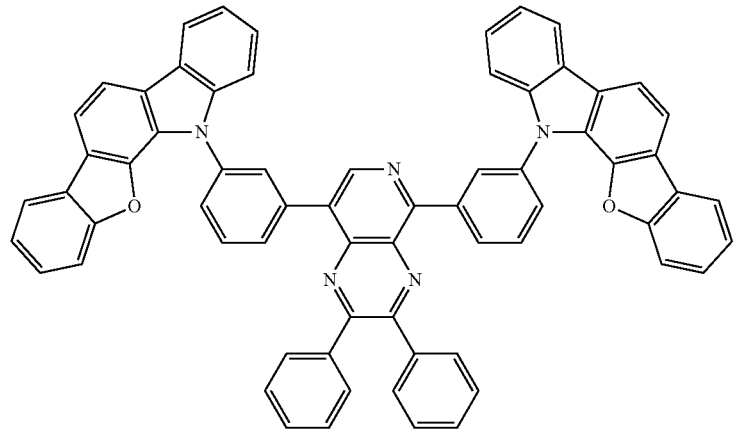
C41
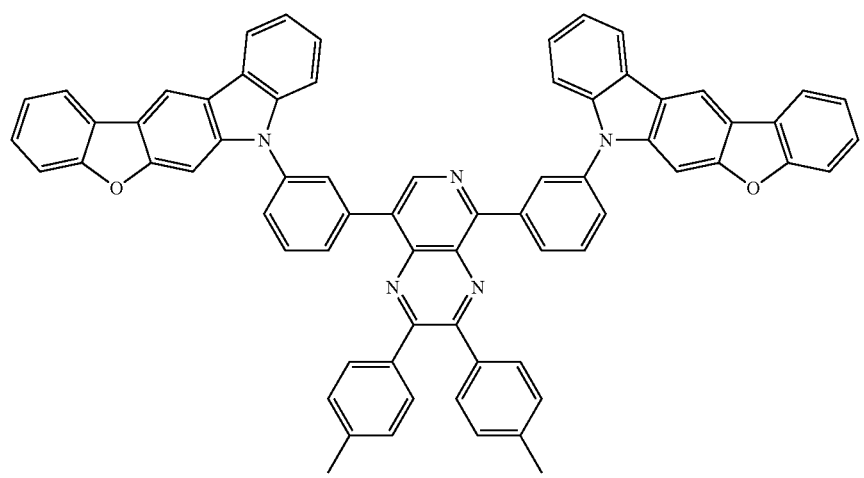
C42
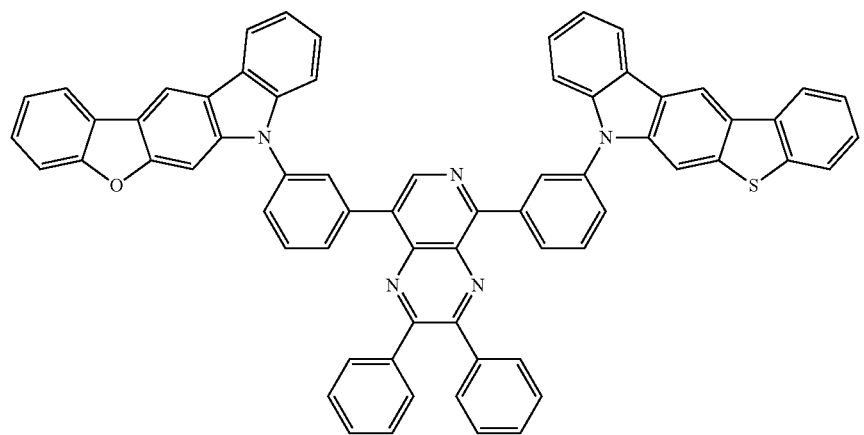
C43

-continued
C44
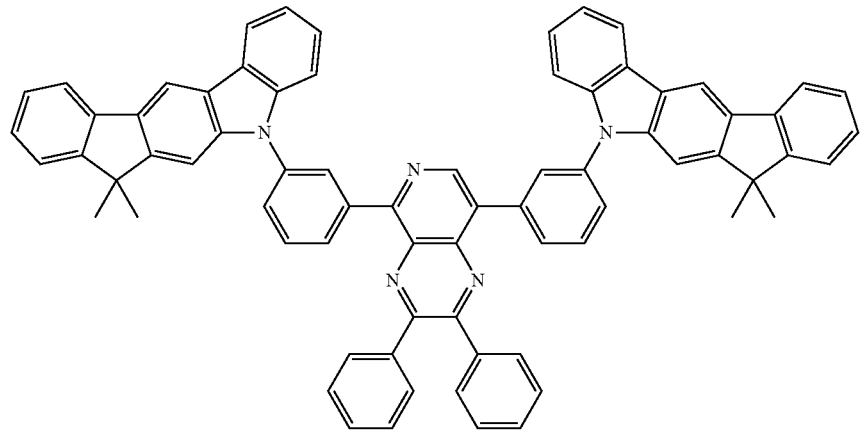
C45
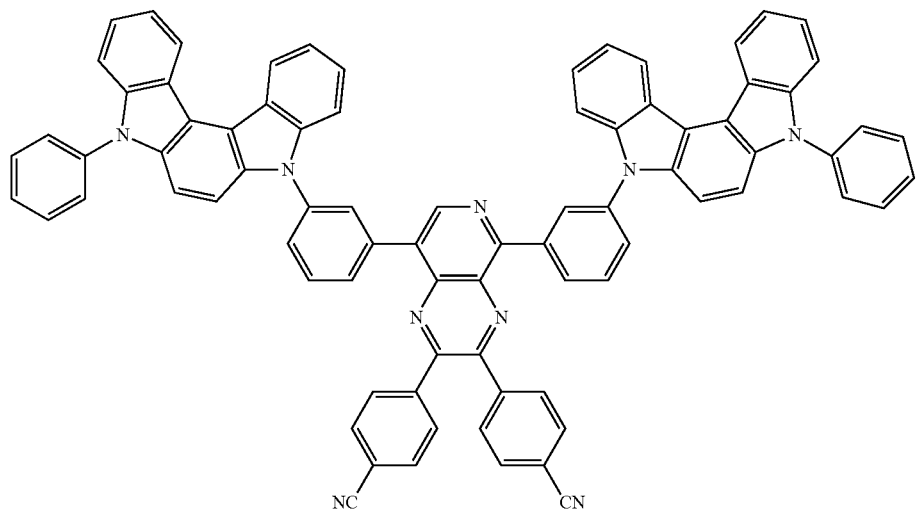
C46
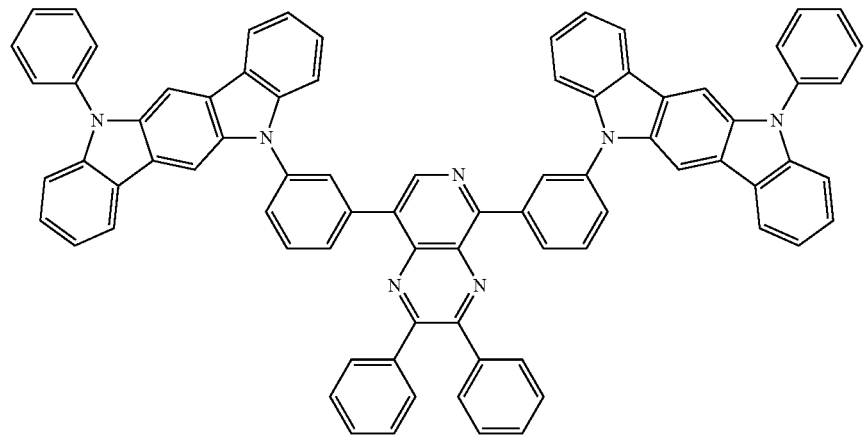

-continued
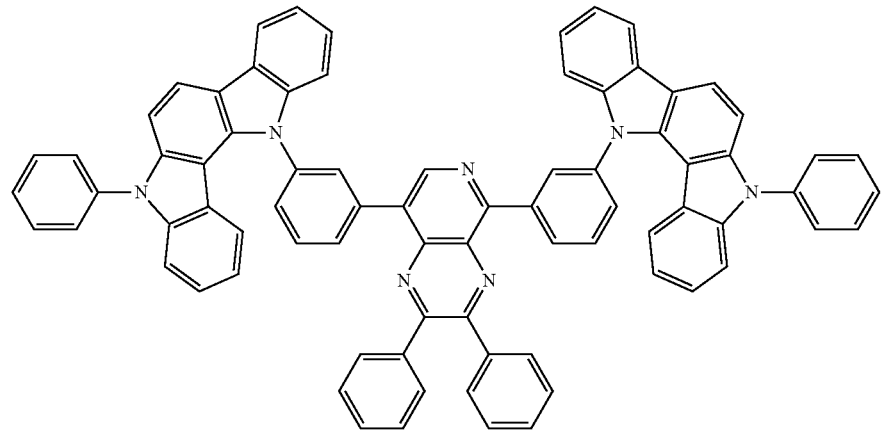
C47
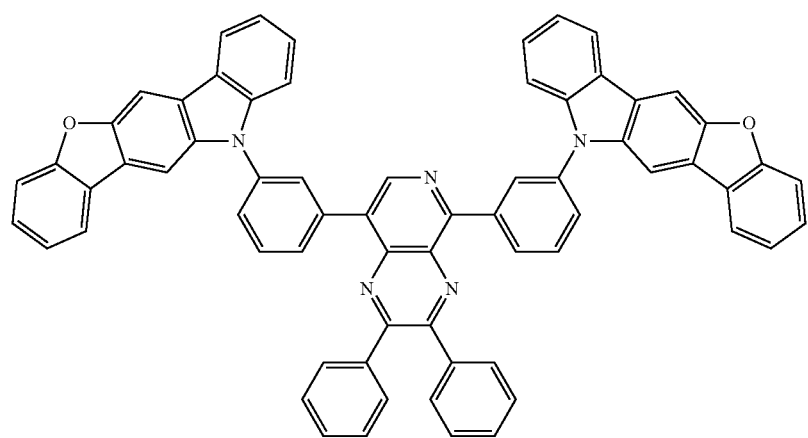
C48
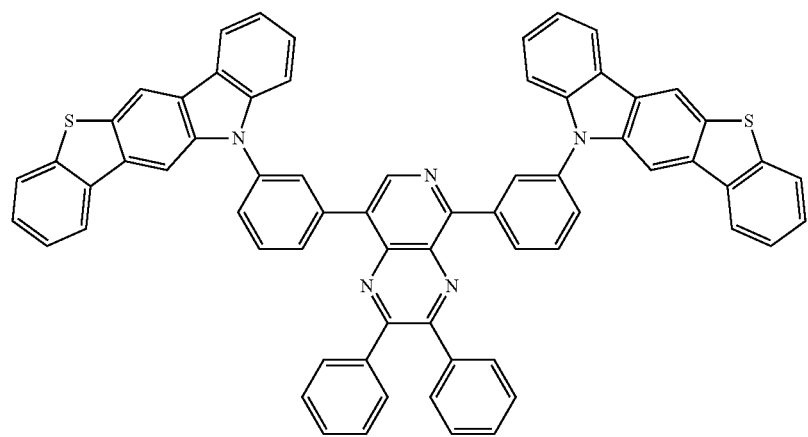
C49

-continued
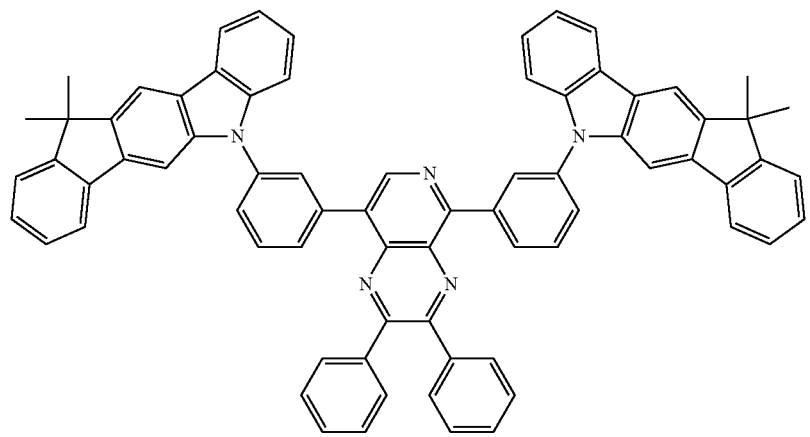
C50
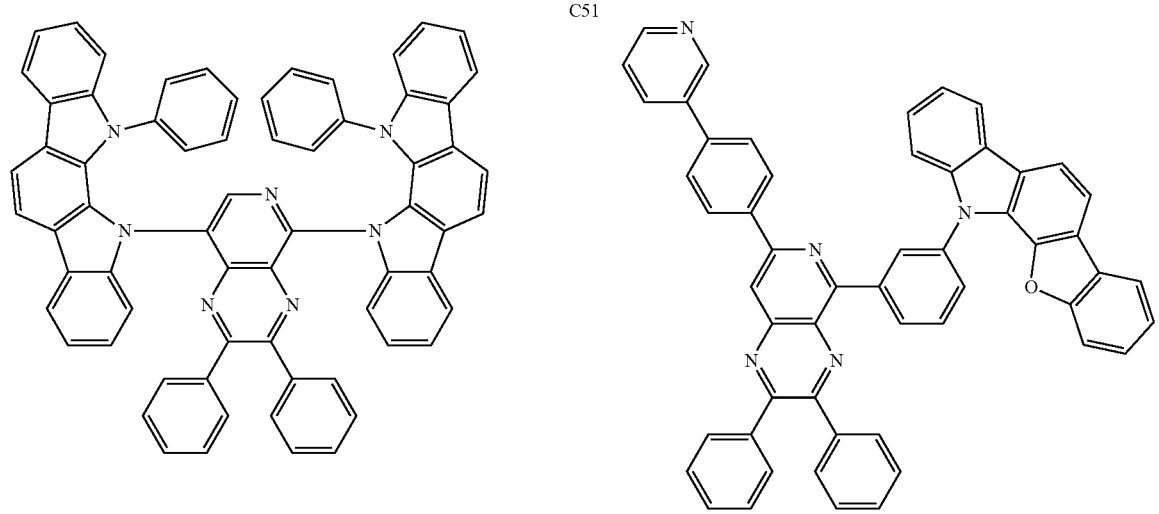
C51 C52
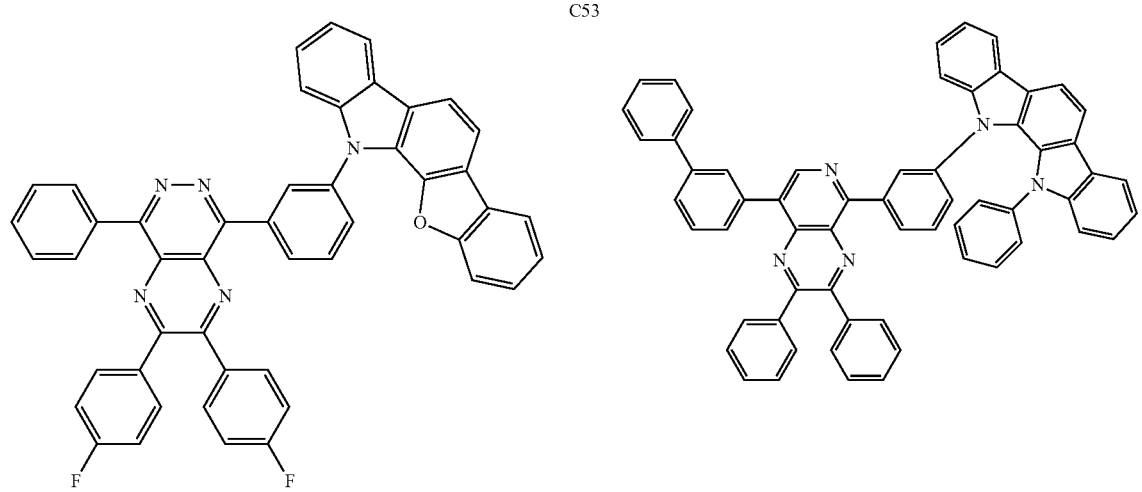
C53 C54

-continued
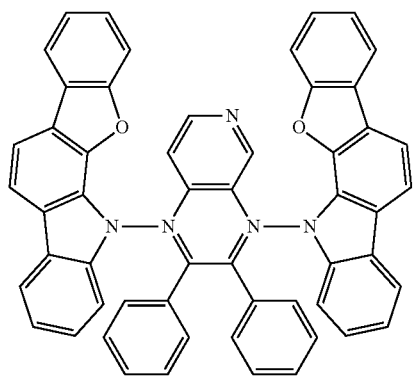
C55
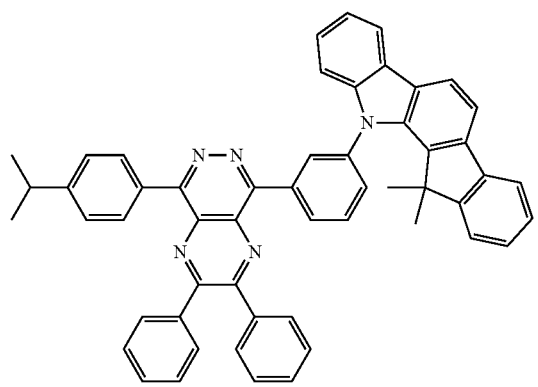
C56
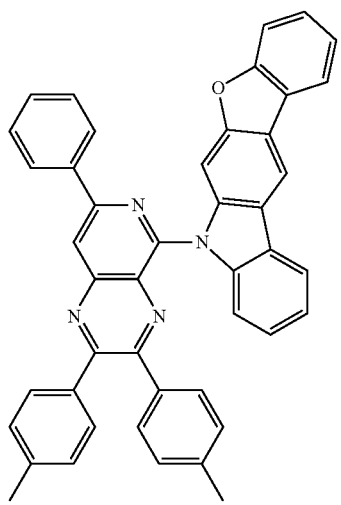
C57
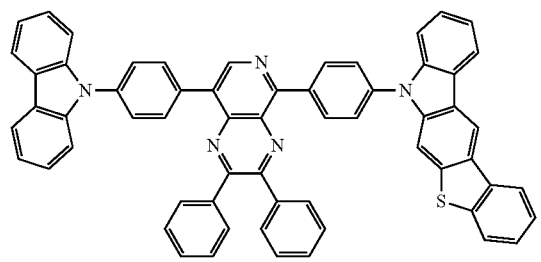
C58
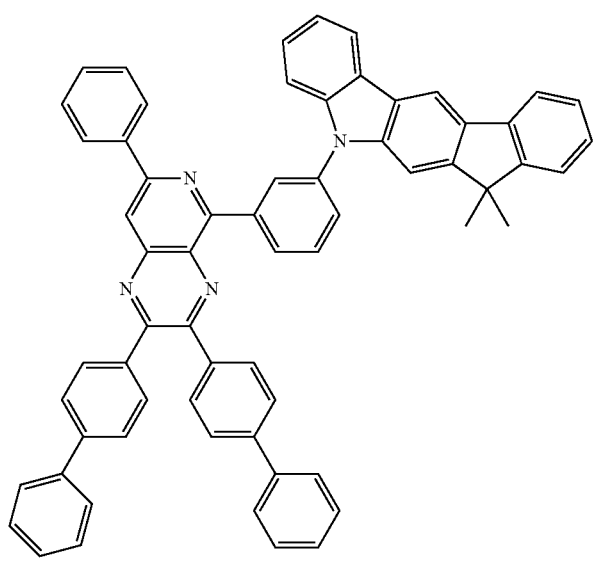
C59

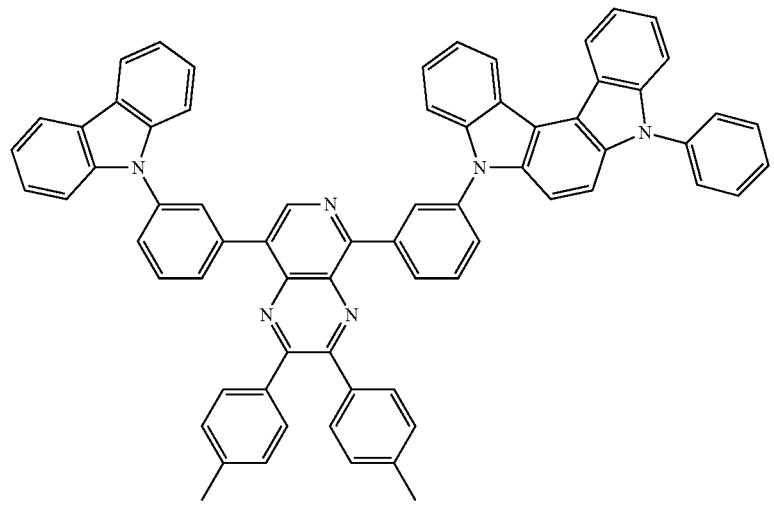
C60
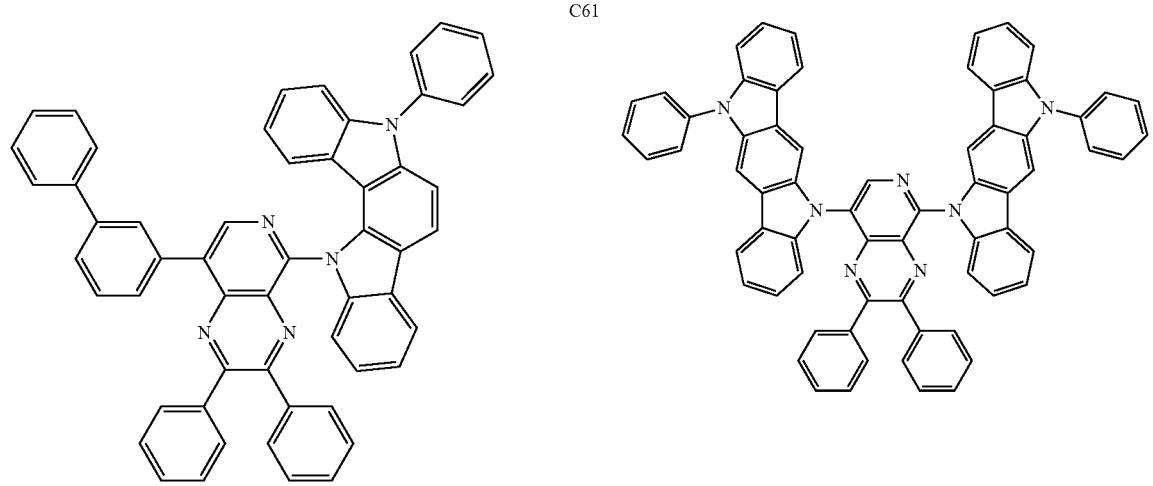
C61 C62
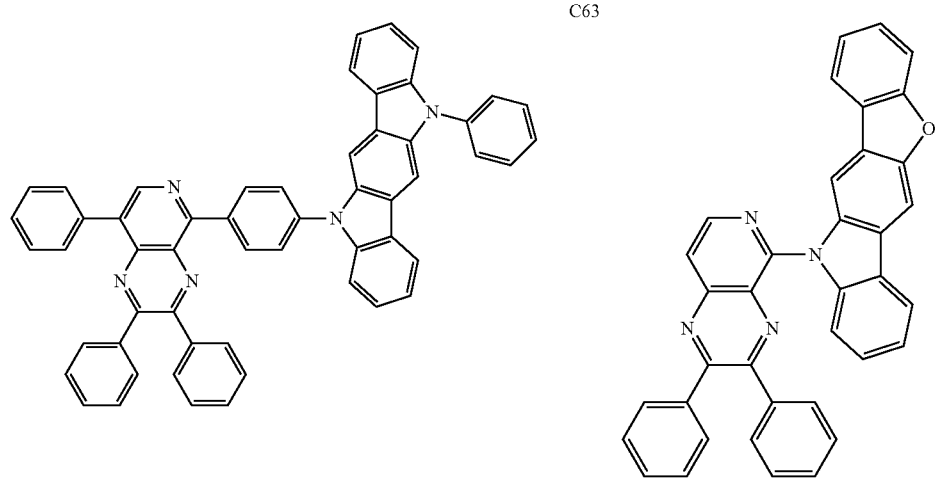
C63 C64

-continued
C65
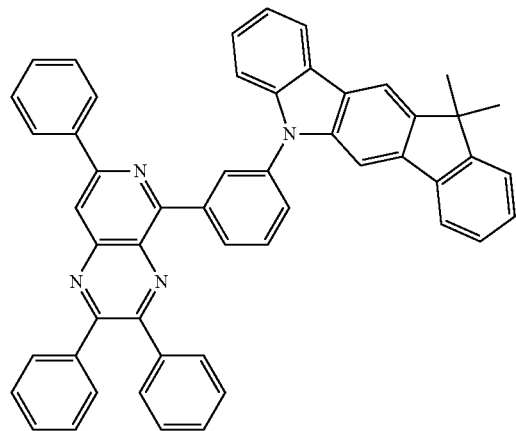
C66
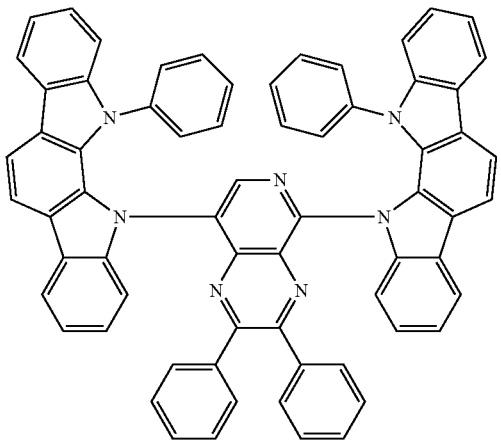
C67
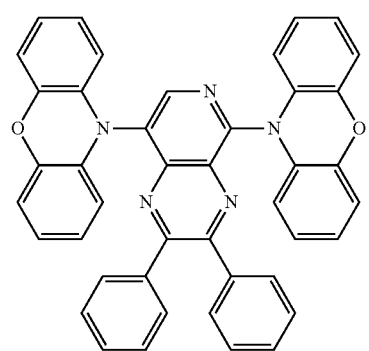
C68
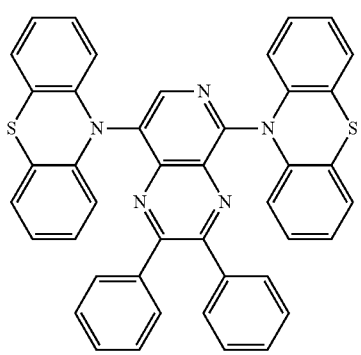
C69
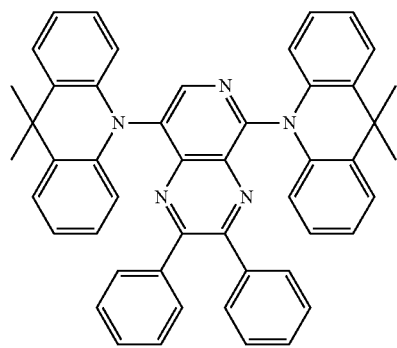
C70
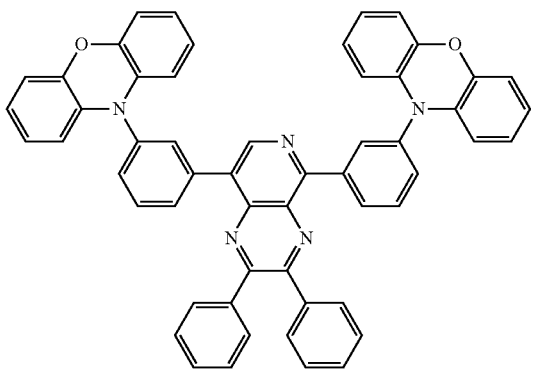
C71
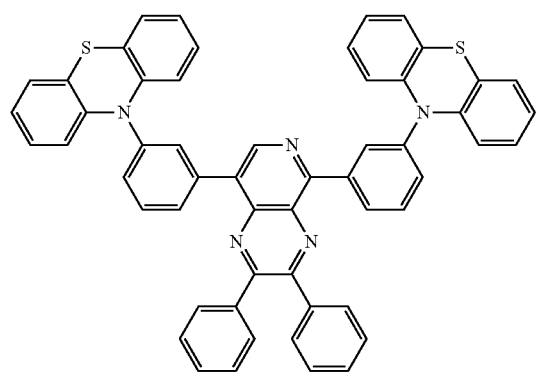
C72
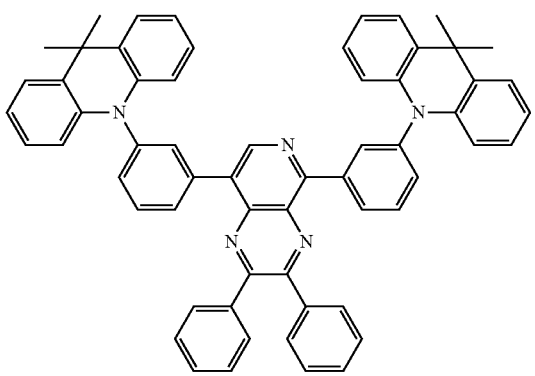

C73
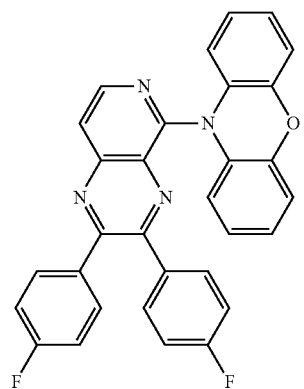

C74
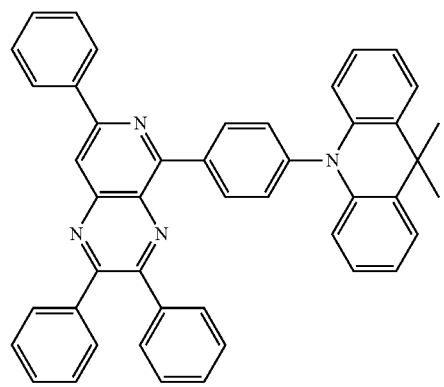

C75
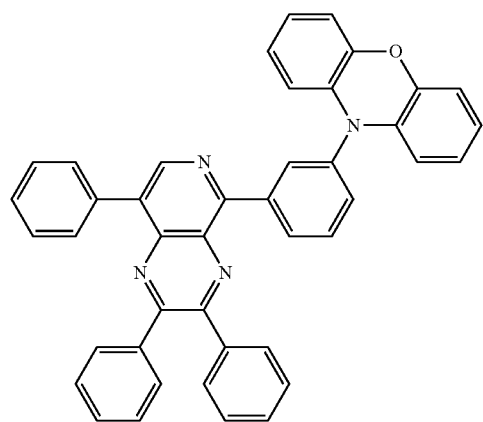

C76
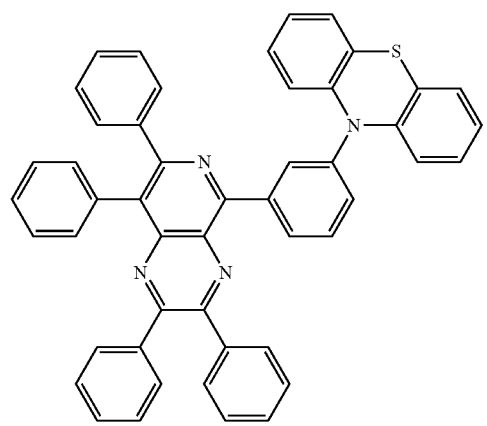

Detailed preparation for the delayed fluorescence compound in the present invention could be clarified by exemplary embodiments, but the present invention is not limited to exemplary embodiments. EXAMPLE 1 to EXAMPLE 6 show the preparation for examples of the delayed fluorescence compound in the present invention. EXAMPLE 10 and 11 show the fabrication of organic EL device and I-V-B, half-life time of organic EL device testing report.

Example 1

Synthesis of C4

Synthesis of 5,8-dibromo-2,3-diphenylpyrido[3,4-b]pyrazine

A mixture of 10 g (37.5 mmol) of 2,5-dibromopyridine-3,4-diamine and 8.66 g (41.2 mmol) of benzil, 200 ml of acetic acid was heated at 100° C. for 2 h. The resulting mixture was allowed to cool to room temperature, and then filtered to get the yellow solid, yield (11 g, 66.7%). 1H NMR (CDCl3, 400 MHz): chemical shift (ppm) 8.50 (s, 1H), 7.41-7.51 (m, 10H).

Synthesis of 9,9'-(2,3-diphenylpyrido[3,4-b]pyrazine-5,8-diyl)bis(9H-carbazole) (C4)

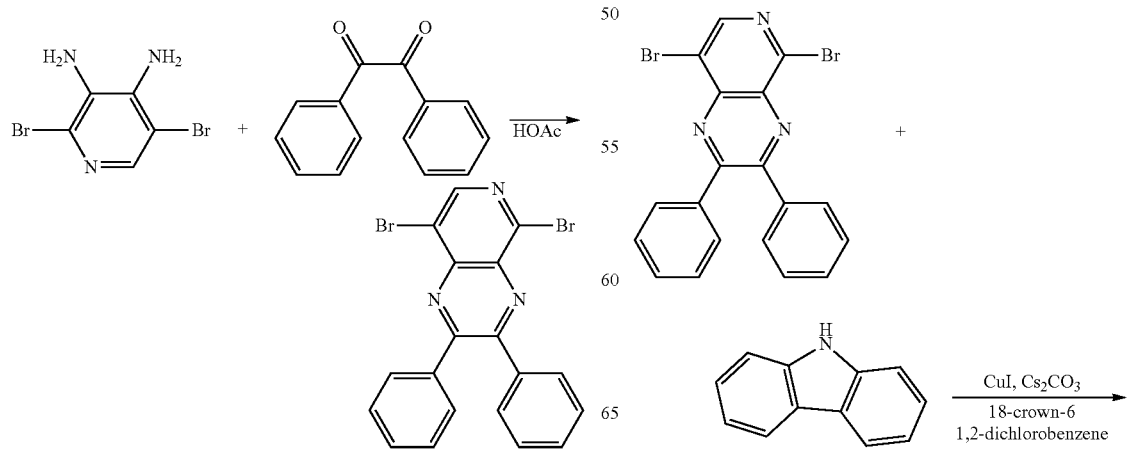

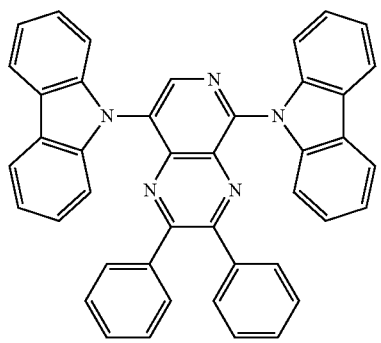

A mixture of 5 g (11.3 mmol) of 5,8-dibromo-2,3-diphenylpyrido [3,4-b]pyrazine and 5.69 g (34 mmol) of carbazole, 2.16 g (11.3 mmol) of CuI, 7.39 g (22.6 mmol) of $Cs_2CO_3$, 2.27 g (8.6 mmol) of 18-crown-6 and 80 ml 1,2-dichlorobenzene was degassed and placed under nitrogen, and then heated to refluex for 12 h. After finishing the reaction, the mixture was allowed to cool to room temperature. The 250 mL of methanol was added, then filtered and washed by methanol to get the red solid, yield (4.5 g, 64.7%). 1H NMR (CDCl3, 400 MHz): chemical shift (ppm) 8.62 (s, 1H), 8.58 (d, 2H), 8.15 (d, 2H), 7.92 (d, 2H), 7.65 (d, 2H), 7.41-7.51 (m, 12H), 7.25-7.33 (m, 6H). MS (m/z, EI$^+$): 613.5

Example 2

Synthesis of C8

Synthesis of 9,9'-(3,3'-(2,3-diphenylpyrido[3,4-b]pyrazine-5,8-diyl)bis(3,1-phenylene))bis(9H-carbazole) (C8)

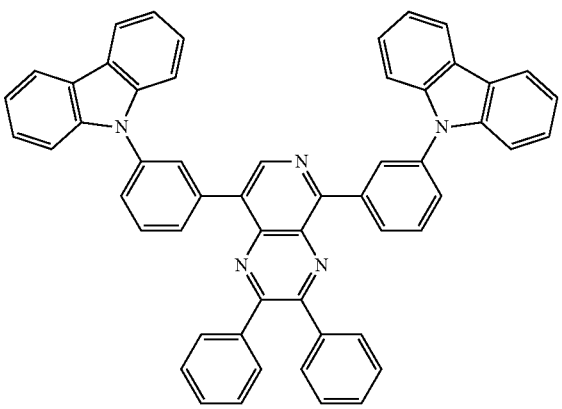

A mixture of 5 g (11.3 mmol) of 5,8-dibromo-2,3-diphenylpyrido [3,4-b]pyrazine and 7.16 g (24.9 mmol) of 3-(9H-carbazol-9-yl) phenylboronic acid, 0.13 g (0.11 mmol) of Pd(PPh$_3$)$_4$, 14.1 ml of 2M Na$_2$CO$_{3(aq)}$, 50 ml of EtOH and 150 ml toluene was degassed and placed under nitrogen, and then heated at 100° C. for 12 h. After finishing the reaction, the mixture was allowed to cool to room temperature. The 250 mL of methanol was added, then filtered and washed by methanol to get the red solid, yield (5.04 g, 59%). MS (m/z, EI$^+$): 765.5

Example 3

Synthesis of C17

Synthesis of 9,9',9'',9'''-(5,5'-(2,3-diphenylpyrido[3,4-b]pyrazine-5,8-diyl)bis(benzene-5,3,1-triyl))tetrakis(9H-carbazole) (C17)

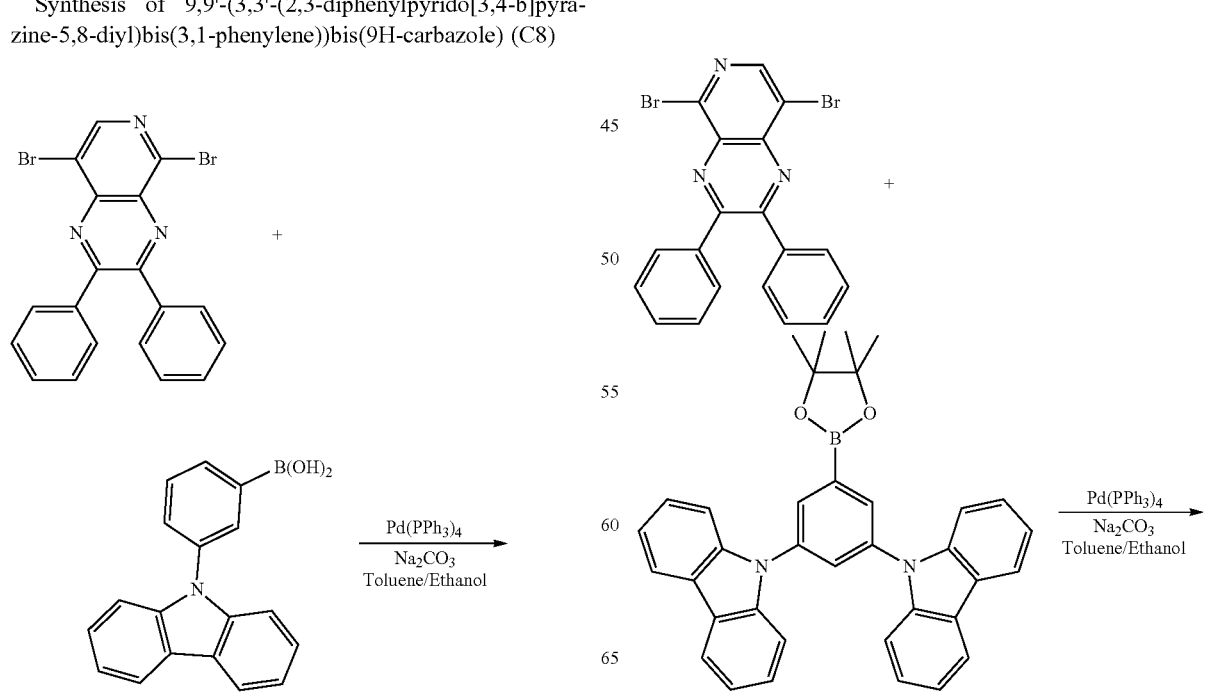

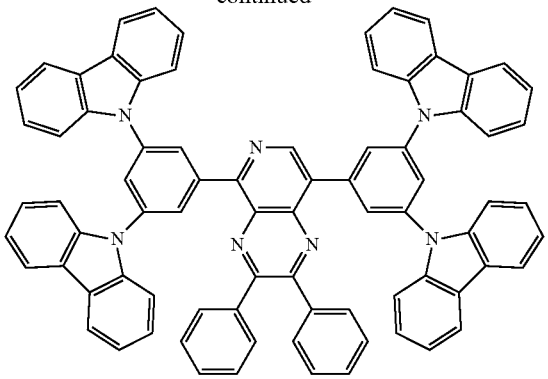

9,9'-(5-(4,4,5,5-tetramethyl-1,3,2-dioxaborolan-2-yl)-1,3-phenylene)bis(9H-carbazole) instead of 3-(9H-carbazol-9-yl) phenyl-boronic acid, except for using the same method as in synthesis Example 2, the desired compound of 9,9',9'',9'''-(5,5'-(2,3-diphenylpyrido[3,4-b]pyrazine-5,8-diyl)bis(benzene-5,3,1-triyl))tetrakis(9H-carbazole) (C17) was obtained. MS (m/z, EI⁺): 1096.4

Example 4

Synthesis of C25

Synthesis of 9,9'-(2,3-diphenylpyrido[3,4-b]pyrazine-5,8-diyl)bis(6-(9H-carbazol-9-yl)-9H-3,9'-bicarbazole) (C25)

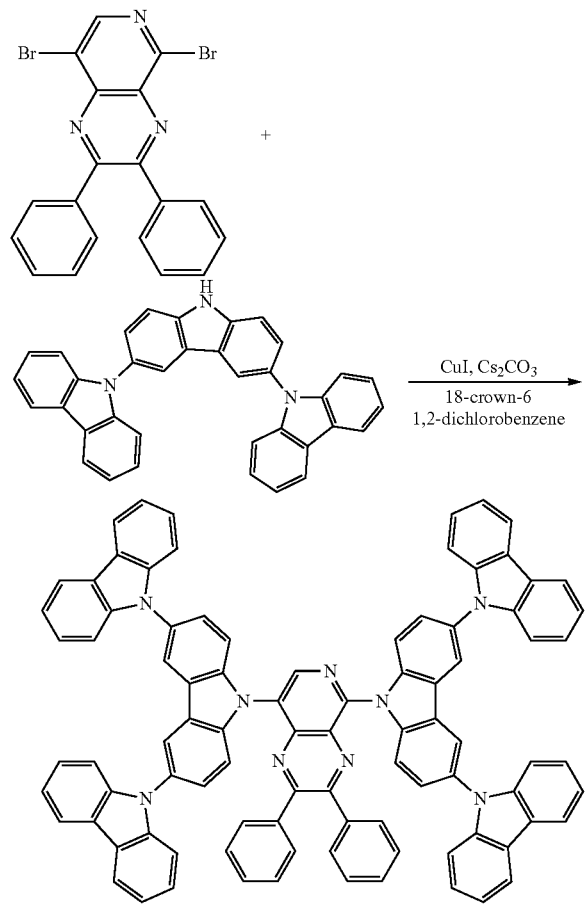

6-(9H-carbazol-9-yl)-9H-3,9'-bicarbazole instead of carbazole, except for using the same method as in synthesis Example 1, the desired compound of 9,9'-(2,3-diphenylpyrido [3,4-b]pyrazine-5,8-diyl)bis(6-(9H-carbazol-9-yl)-9H-3,9'-bicarbazole) (C25) was obtained. MS (m/z, EI⁺): 1274.8

Example 5

Synthesis of C38

Synthesis of 12,12'-(3,3'-(2,3-diphenylpyrido[3,4-b]pyrazine-5,8-diyl)bis(3,1-phenylene))bis(11-phenyl-11,12-dihydroindolo[2,3-a]carbazole) (C38)

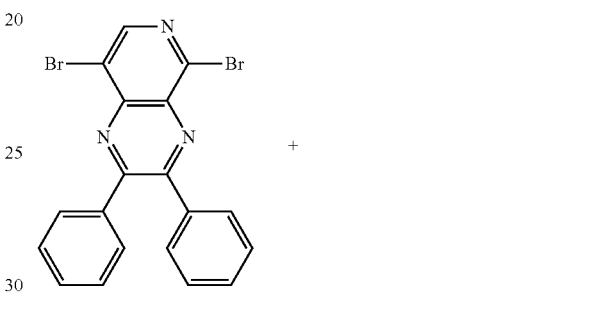

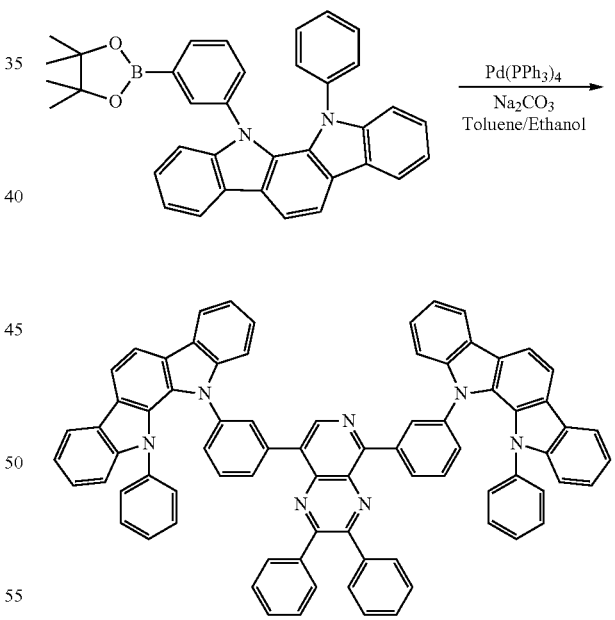

11-phenyl-12-(3-(4,4,5,5-tetramethyl-1,3,2-dioxaborolan-2-yl) phenyl)-11,12-dihydroindolo[2,3-a]carbazole instead of 3-(9H-carbazol-9-yl) phenylboronic acid, except for using the same method as in synthesis Example 2, the desired compound of 12,12'-(3,3'-(2,3-diphenylpyrido[3,4-b]pyrazine-5,8-diyl)bis(3,1-phenylene))bis(11-phenyl-11,12-dihydroindolo[2,3-a]carbazole) (C38) was obtained. MS (m/z, EI⁺): 1096.6

Example 6

Synthesis of C67

Synthesis of 10,10'-(2,3-diphenylpyrido[3,4-b]pyrazine-5,8-diyl)bis(10H-phenoxazine) (C67)

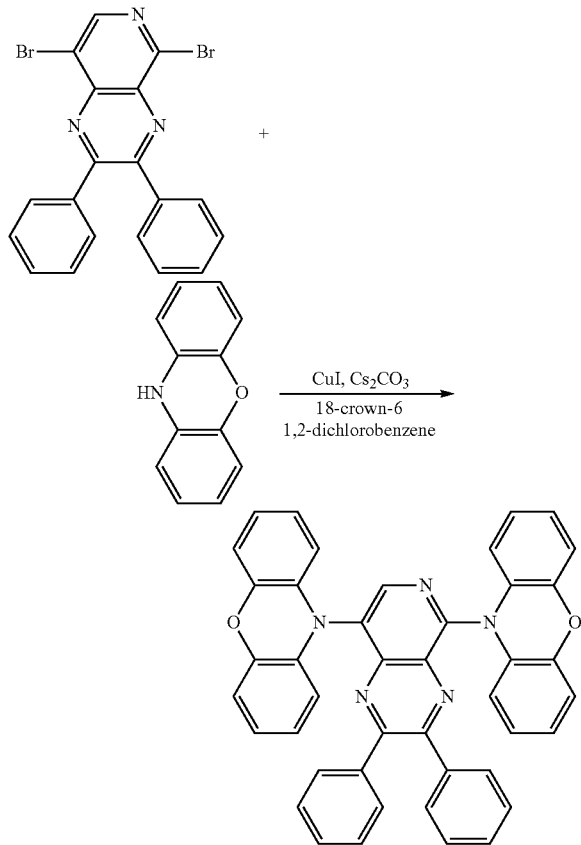

10H-phenoxazine instead of carbazole, except for using the same method as in synthesis Example 1, the desired compound of 10,10'-(2,3-diphenylpyrido[3,4-b]pyrazine-5,8-diyl)bis(10H-phenoxazine) (C67) was obtained. MS (m/z, EI$^+$): 645.3

Measurement Method of Delayed Fluorescence Compound for Photophysical Properties Photophysical Characterization: Synthesized compounds were subject to purification by temperature-gradient sublimation in high vacuum before use in subsequent studies. Thin films for photophysical characterization were prepared by thermal evaporation on quartz substrates at 1-2 A/sec in a vacuum chamber with a base pressure of <10-6 torr. Absorption spectra of the resulting thin films and dilute solutions were characterized by a UV-vis-NIR spectrophotometer (UV-1650 PC, Shimadzu). Photoluminescence (PL) spectra, photoluminescence quantum yields (PLQYs), and phosphorescence spectra were characterized by a spectrofluorimeter (FluoroMax-P, Horiba Jobin Yvon Inc.). PLQYs of thin films or dilute solutions were determined using this spectrofluorimeter equipped with a calibrated integrating sphere. The selected monochromatic excitation light was used to excite samples placed in the calibrated integrating sphere. By comparing the spectral intensities of the monochromatic excitation light and the PL emission, the PL quantum yields were determined. Phosphorescence spectra of thin films or dilute solutions were conducted at 77K (the liquid nitrogen temperature) by the spectrofluorometer equipped with a microsecond flash lamp as the pulsed excitation source. A 10-ms delay time was inserted between the pulsed excitation and the collection of the emission spectrum. Time-resolved PL (PL decay curves) was measured by monitoring the decay of the intensity at the PL peak wavelength using the time-correlated single-photon counting technique with a fluorescence lifetime system (FluoroCube, Horiba Jobin Yvon Inc.) and nanosecond pulsed light excitation from a UV light-emitting diode (300 nm). The samples were placed in a vacuum cryostat chamber with the temperature control. The PL spectra of the prompt and delayed components were collected using this same fluorescence lifetime system with a 200-ns delay time and a 10-us delay time between the pulsed excitation and the collection of the emission spectrum. Electrochemical Characterization: Cyclic voltammetry by a CHI 619B potentiostat was used to measure oxidation/reduction potentials. The oxidation potential was determined by cyclic voltammetry (CV) using 0.1M n-Bu4NPF6 (TBAPF6) in CH2Cl2 as a supporting electrolyte and a scan rate of 100 mV s−1. The reduction potential was recorded using 0.1M n-Bu4NClO4 (TBAP) in DMF as a supporting electrolyte and a scan rate of 100 mV s−1. A standard 3-electrode cell comprising silver/silver chloride (Ag/AgCl), a platinum wire and a glassy carbon electrode as the reference, counter, and working electrodes, respectively, were used. All potentials were recorded versus Ag/AgCl (saturated) as a reference electrode. Oxidation of the ferrocene/ferrocenium (Fc/Fc+) redox couple in CH2Cl2/TBAPF6 occurs at E'o=+0.47V and reduction of the ferrocene/ferrocenium (Fc/Fc+) redox couple in DMF/TBAP occurs at E"o=+0.51 V vs. Ag/AgCl (saturated) collecting the total emission fluxes with a calibrated integrating-sphere measurement system.

Figure 2:
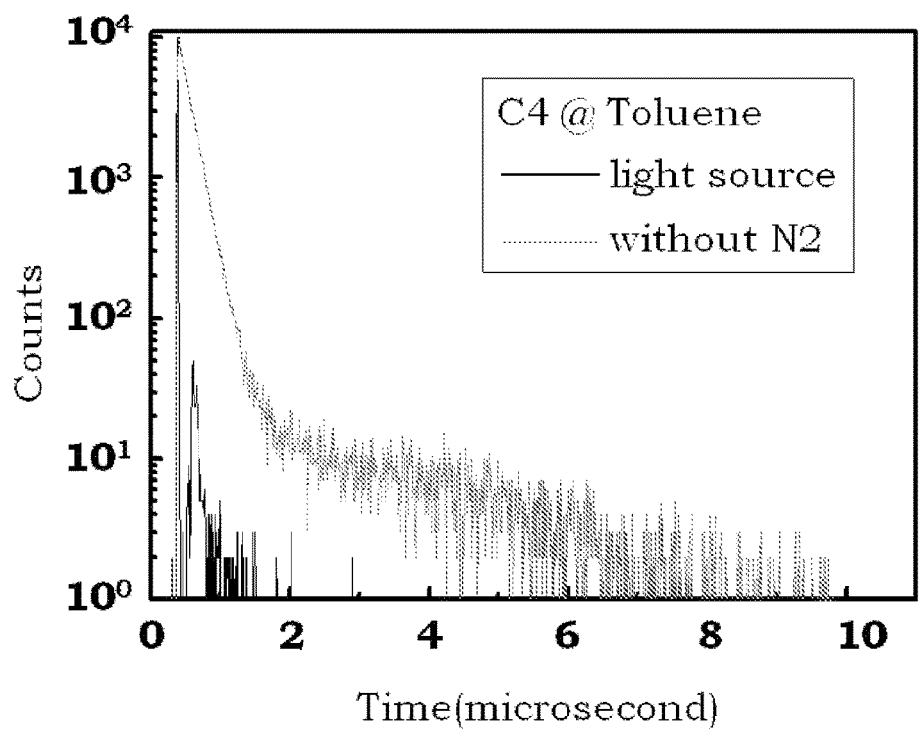
FIG. 2 show the transient decay cure of compound C4 for the delayed fluorescent property.
Figure 2:
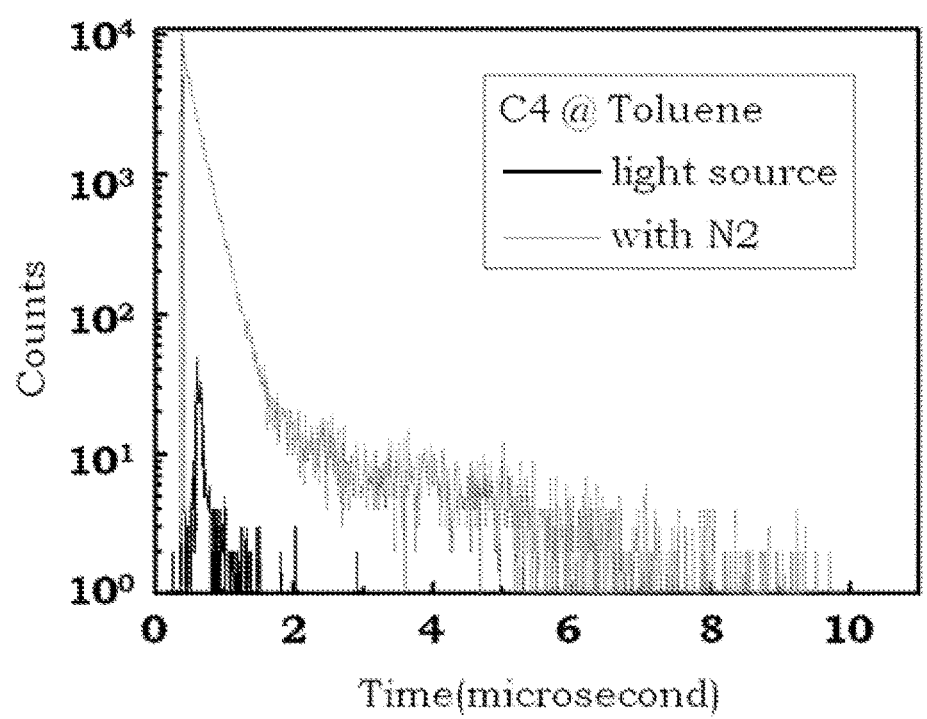
Figure 3:
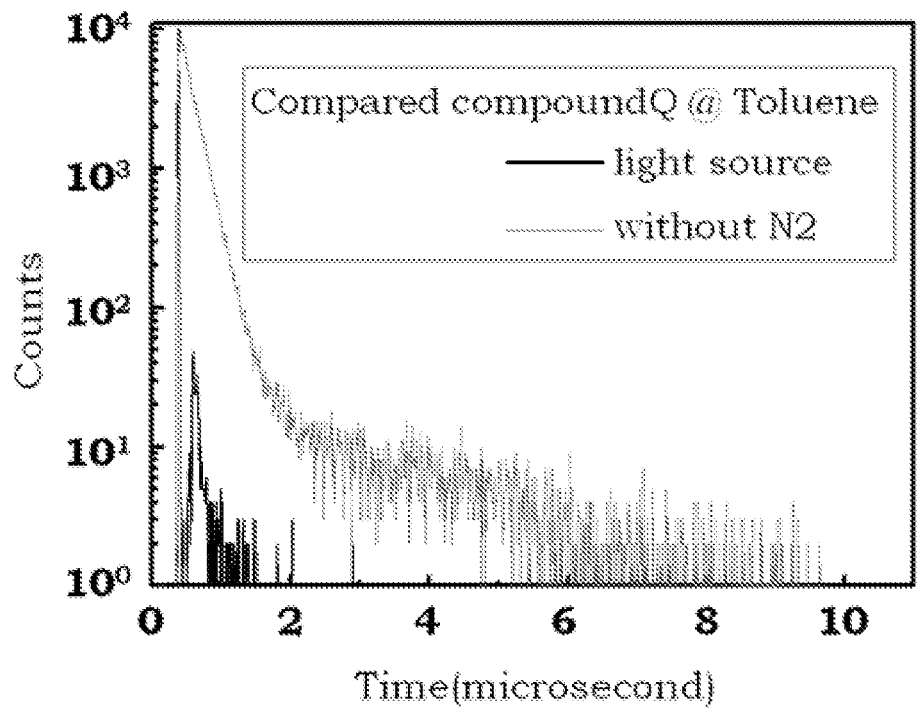
FIG. 3 show the transient decay cure of compared compound Q for the delayed fluorescent property.
Figure 3:
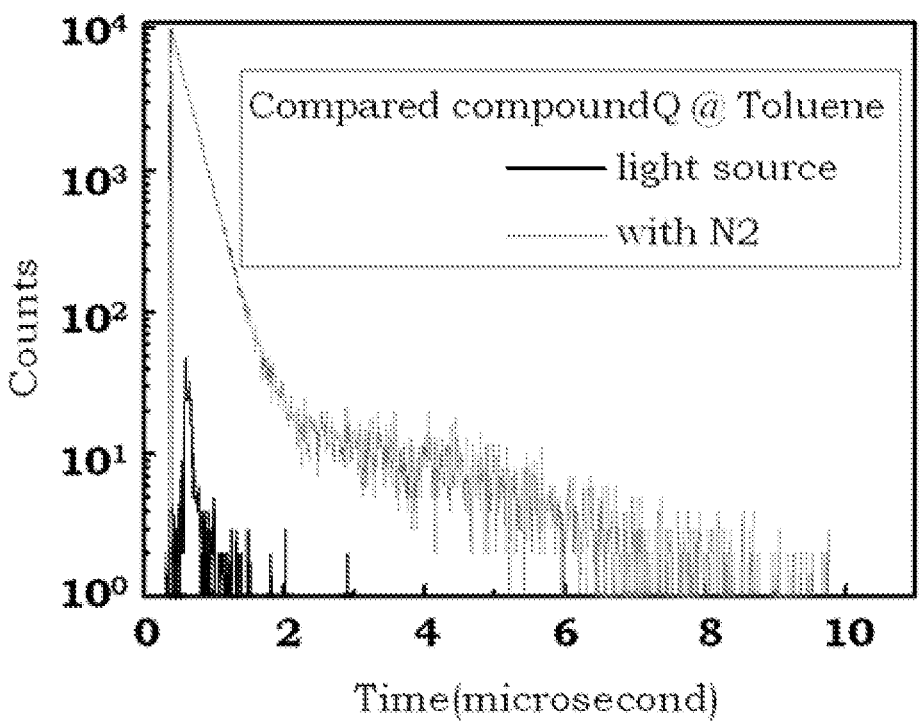
Figure 4:
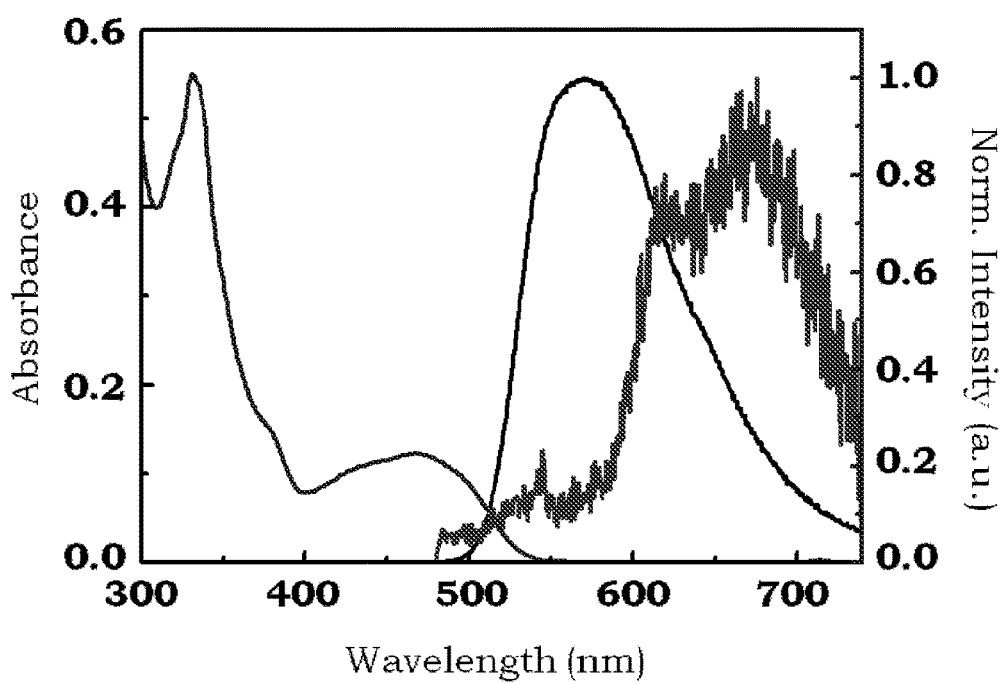
FIG. 4 show the of UV-Vis (nm) and PL (nm) graphs of compound C4.
Figure 5:
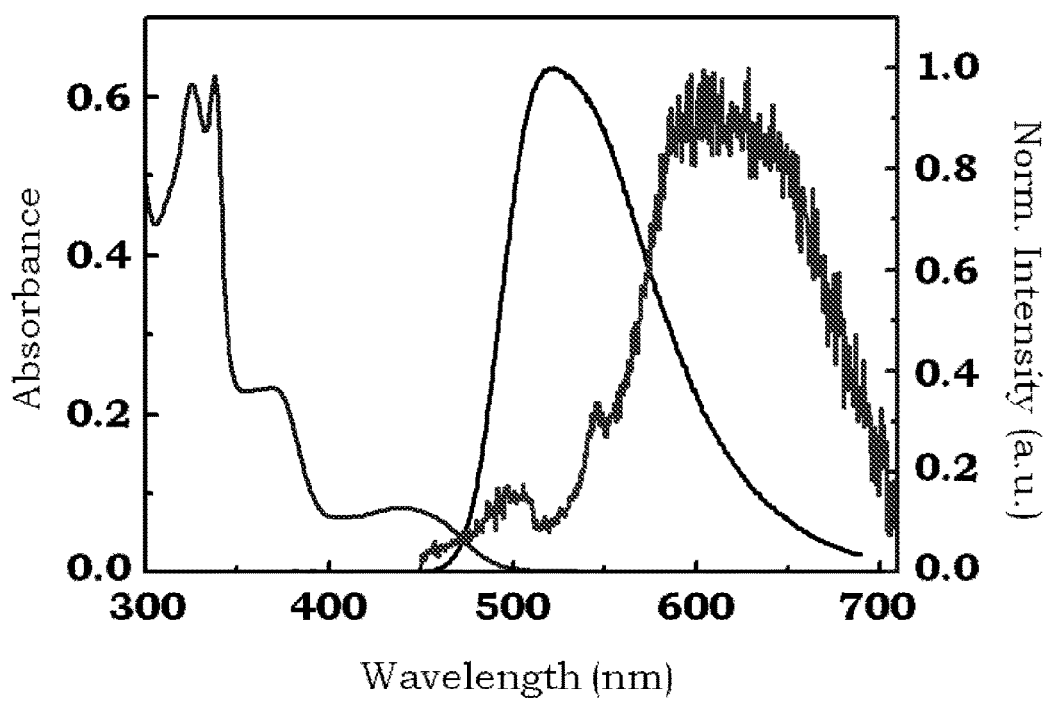
FIG. 5 show the of UV-Vis (nm) and PL (nm) graphs of compared compound Q.

FIG. 2 and FIG. 3 show the measurement of the transient decay curve of Toluene solution had displayed delayed fluorescence for C4 and Compared compound. FIG. 4 and FIG. 5 show the measurement of the photoluminescence light emission spectrum of C4 and Compared compound.

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^7$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3f:2,3-]quinoxaline-2,3,6,7,10,11-hexacarbonitrile (HAT-CN) is used as hole injection layer in this organic EL device, and N4,N4'-di(biphenyl-4-yl)-N4,N4'-diphenylbiphenyl-4,4'-diamine (HT1) is used as the hole transporting layer, N-(biphenyl-4-yl)-9,9-dimethyl-N-(4'-phenyl biphenyl-4-yl)-9H-fluoren-2-amine (EB2) is used as electron blocking layer, H1 used as phosphorescent host and delayed fluorescence host for comparable or standard with the present invention. The chemical structure shown below:

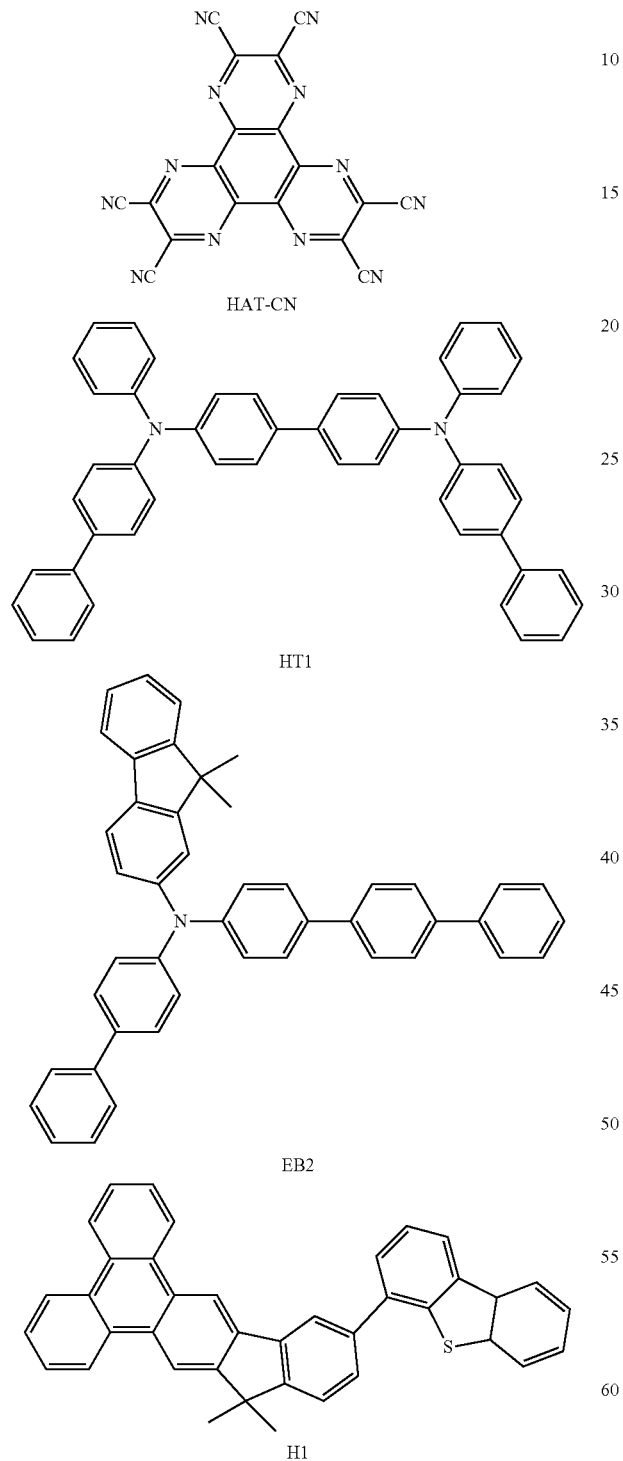

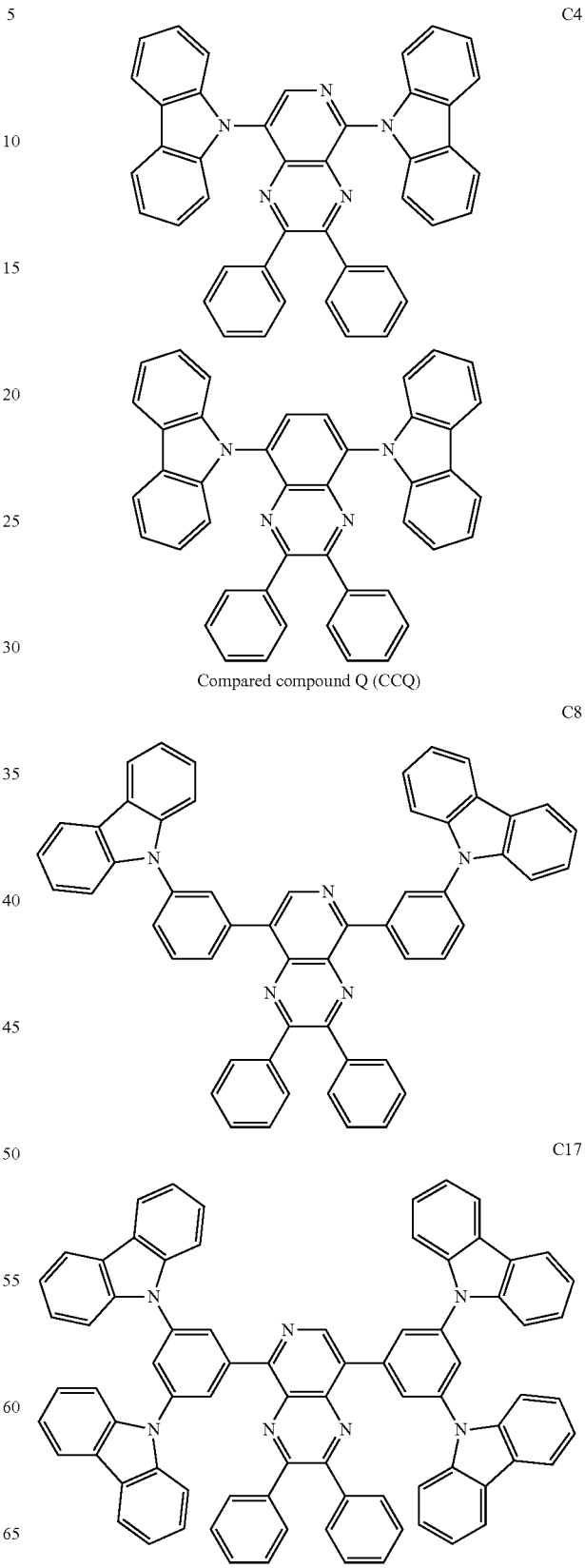

device. Compared compound Q (CCQ) is used as delayed fluorescence dopant for compared compound in the present invention.

The following delayed fluorescence Examples prepared in the present invention can be verified and used as delayed fluorescence dopant, phosphorescence host, hole blocking material or electron transporting material by organic EL -continued

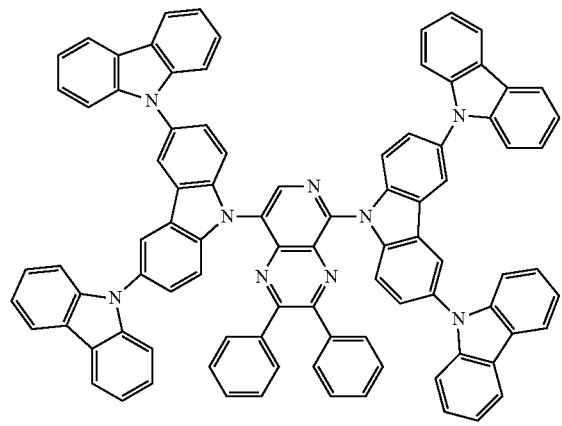

C25

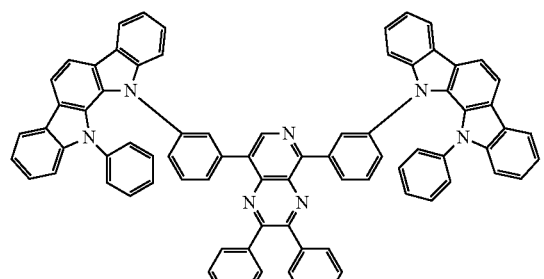

C38

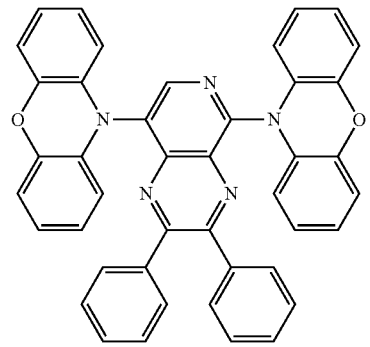

C67

Organic iridium complexes are widely used as phosphorescent dopant for light emitting layer, Ir(ppy)₃ are widely used for phosphorescent green dopant of light emitting layer for organic EL device.

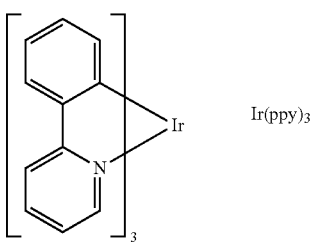

Ir(ppy)₃

2,2',2"-(1,3,5-Benzinetriyl)-tris(1-phenyl-1-H-benzimidazole) (TPBi) and HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

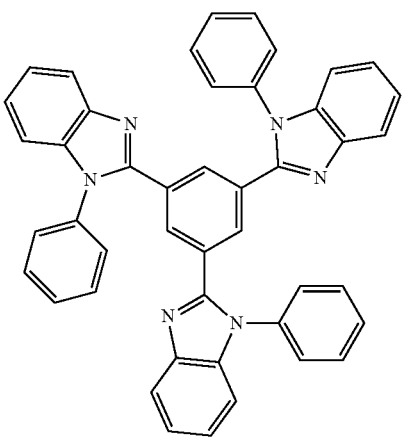

TPBi

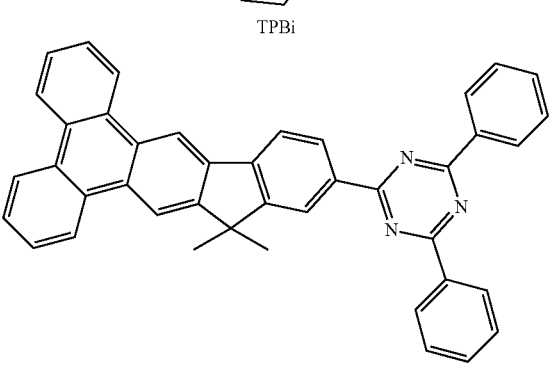

ET2

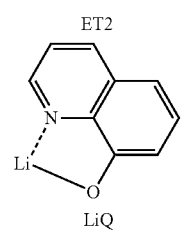

LiQ

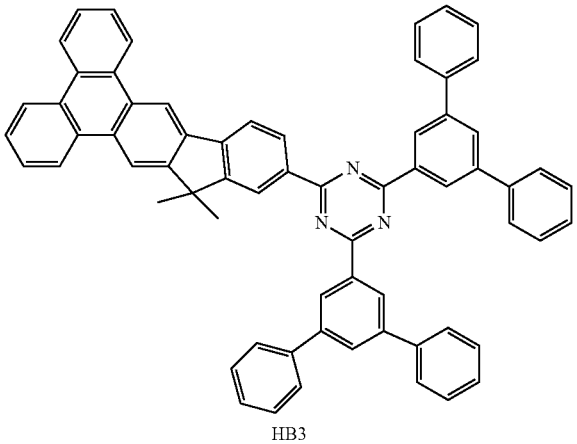

HB3

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 10

Using a procedure analogous to the above mentioned general method, organic EL device having the following device structure was produced (See FIG. 1). Device: ITO/HAT-CN (20 nm)/HT1 (110 nm)/EB2 (5 nm)/Host+ 10%~30% dopant (30 nm)/HBM (10 nm)/ETM doped 40% LiQ (35 nm)/LiQ (1 nm)/Al (160 nm). The I-V-B (at 1000 nits) of organic EL device testing report as Table 1.

TABLE 1

| Dopant (%) | Host | HBM | ETM | Voltage (V) | Efficiency (cd/A) |
|---|---|---|---|---|---|
| C4(30%) | H1 | TPBi | ET2 | 6.2 | 16 |
| CCQ(30%) | H1 | TPBi | ET2 | 7.5 | 9 |
| C8(35%) | H1 | TPBi | ET2 | 6.5 | 14 |
| C67(35%) | H1 | TPBi | ET2 | 5.8 | 18 |
| Ir(ppy)$_3$(8%) | H1 | HB3 | ET2 | 4.2 | 24 |
| Ir(ppy)$_3$(8%) | C38 | HB3 | ET2 | 4.8 | 28 |
| Ir(ppy)$_3$(8%) | H1 | C17 | ET2 | 5.0 | 20 |
| Ir(ppy)$_3$(8%) | H1 | C25 | ET2 | 5.0 | 23 |
| Ir(ppy)$_3$(8%) | H1 | HB3 | C4 | 5.5 | 16 |
| Ir(ppy)$_3$(8%) | H1 | HB3 | C8 | 4.8 | 19 |

In the above preferred embodiments for organic EL device testing report (see Table 1), we show that the delayed fluorescence compound with a general formula (1) used as light emitting host of emitting layer, and/or an electron transporting layer, and/or a hole blocking layer, and/or a delayed fluorescence (TADF) material of emitting layer for organic EL device in the present invention display good performance than the prior art of organic EL materials. Especially 2,3-diphenylpyrido[3,4-b]pyrazine skeleton (such as C4) used as delayed fluorescence compound for organic EL device shown better efficiency than quinoxaline core (such as CCQ).

To sum up, the present invention discloses an delayed fluorescence compound which can be used as phosphorescent light emitting host of emitting layer, and/or an electron transporting layer, and/or a hole blocking layer, and/or a delayed fluorescence material of emitting layer for organic EL device The mentioned delayed fluorescence compound formula (1) represented by the following formula (1)

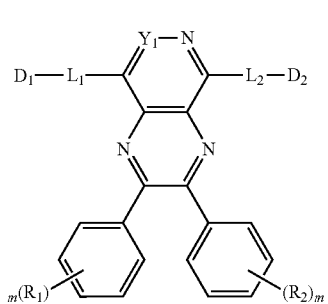

formula(1)

wherein D$_1$ and D$_2$ are independently selected from the group consisting of formula (2) to formula (6):

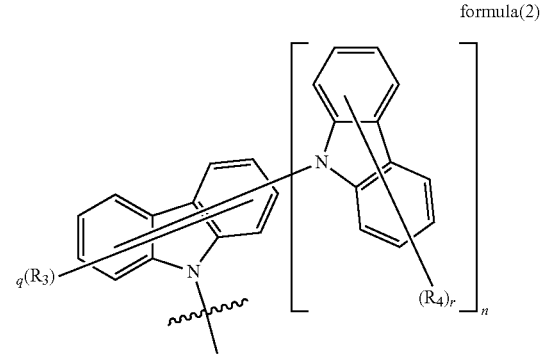

formula(2)

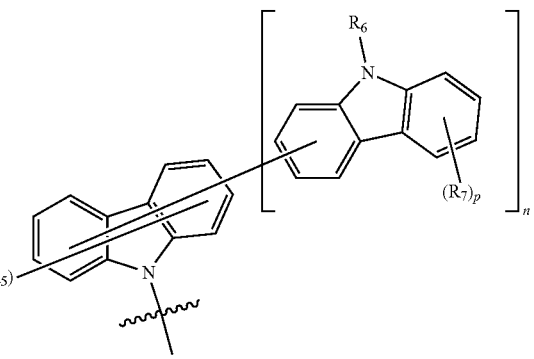

formula(3)

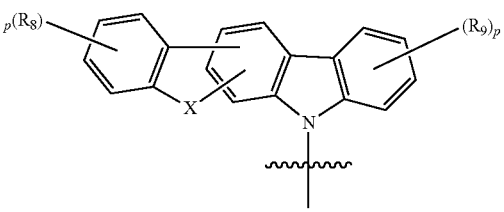

formula(4)

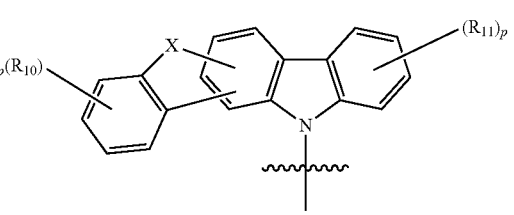

formula(5)

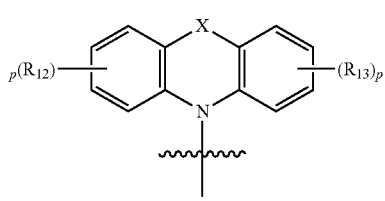
formula(6)

L represents a single bond, a substituted or unsubstituted arylene group having 6 to 30 ring carbon atoms, or a substituted or unsubstituted heterarylene group having 3 to 30 ring carbon atoms, m represent an integer of 0 to 5, n represents an integer of 0 to 2, p represents an integer of 0 to 4, q represents an integer of 0 to 7, r represents an integer of 0 to 8, X is a divalent bridge selected from the atom or group consisting from O, S, $C(R_{14})(R_{15})$, $NR_{16}$ and $Si(R_{17})(R_{18})$, $Y_1$ represents a nitrogen atom or $C(R_s)$, and each $R_s$ represents a hydrogen, a phenyl, a substituted or unsubstituted alkyl group having 1 to 30 carbon atoms, a substituted or unsubstituted aryl group having 6 to 30 carbon atoms; $R_1$ and $R_2$ are independently selected from the group consisting of a hydrogen atom, a halide, a nitro, a pyridine, a pyrazine, a pyrimidine, a triazine, a substituted or unsubstituted alkyl group having 1 to 30 carbon atoms and a substituted or unsubstituted aryl group having 6 to 30 carbon atoms, $R_3$ to $R_{18}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:
1. A delayed fluorescence compound represented by the following formula (1):

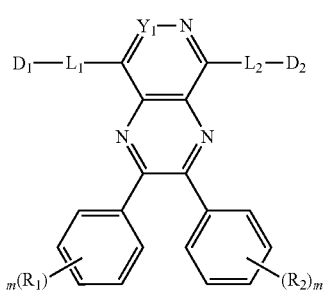
formula(1)

wherein $D_1$ and $D_2$ are independently selected from the group consisting of formula (2) to formula (6):

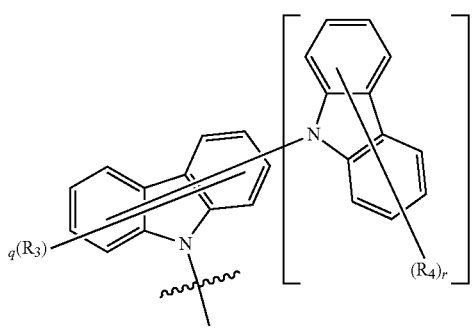
formula(2)

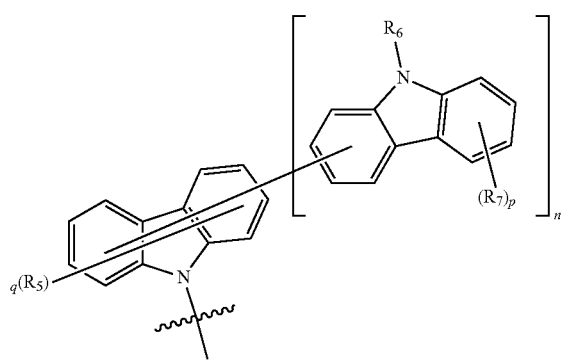
formula(3)

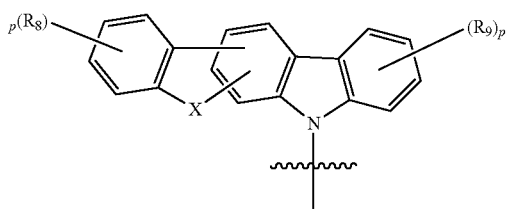
formula(4)

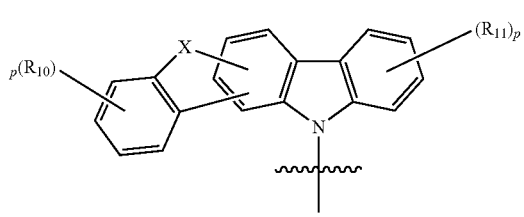
formula(5)

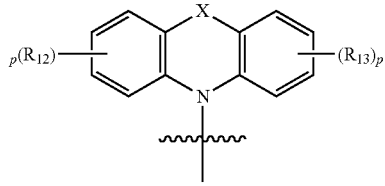
formula(6)

L represents a single bond, a substituted or unsubstituted arylene group having 6 to 30 ring carbon atoms, or a substituted or unsubstituted heterarylene group having 3 to 30 ring carbon atoms, m represent an integer of 0 to 5, n represents an integer of 0 to 2, p represents an integer of 0 to 4, q represents an integer of 0 to 7, r represents an integer of 0 to 8, X is a divalent bridge selected from the atom or group consisting from O, S, $C(R_{14})(R_{15})$, $NR_{16}$ and $Si(R_{17})(R_{18})$, $Y_1$ represents a nitrogen atom or $C(R_s)$, and each $R_s$ represents a hydrogen, a phenyl, a substituted or unsubstituted alkyl group having 1 to 30 carbon atoms, a substituted or unsubstituted aryl group having 6 to 30 carbon atoms; $R_1$ and $R_2$ are independently selected from the group consisting of a hydrogen atom, a halide, a nitro, a pyridine, a pyrazine, a pyrimidine, a triazine, a substituted or unsubstituted alkyl group having 1 to 30 carbon atoms and a substituted or unsubstituted aryl group having 6 to 30 carbon atoms, $R_3$ to $R_{18}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

2. The delayed fluorescence compound according to claim 1, wherein $L_1$ and $L_2$ are represented by the following formula (7):

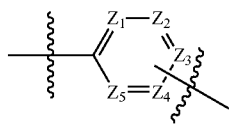

formula(7)

wherein $Z_1$ to $Z_5$ independently represent a nitrogen atom or $C(R_s)$, and each $R_s$ represents a hydrogen, a phenyl, a substituted or unsubstituted alkyl group having 1 to 30 carbon atoms and a substituted or unsubstituted aryl group having 6 to 30 carbon atoms.

3. The delayed fluorescence compound according to claim 1, wherein a difference between a singlet energy of the delayed fluorescence compound and a triplet energy of the delayed fluorescence compound is less than 0.25 eV.

4. The delayed fluorescence compound according to claim 1, wherein the delayed fluorescence compound is a light-emitting material.

5. The light-emitting material according to claim 4, wherein the light-emitting material emits delayed fluorescence.

6. An organic electroluminescence device comprising a pair of electrodes consisting of a cathode and an anode, and between the pairs of electrodes comprising at least a light emitting layer and one or more layers of organic thin film layer, wherein the light emitting layer, one or more layers of organic thin film layer, wherein the light emitting layer and/or the one or more organic thin film layers comprises the delayed fluorescence compound with a general formula (1) according to claim 1.

7. The organic electroluminescence device according to claim 6, wherein a difference between a singlet energy of the delayed fluorescence compound and a triplet energy of the delayed fluorescence compound is less than 0.25 eV.

8. The organic electroluminescence device according to claim 6, wherein the light emitting layer comprises the delayed fluorescence compound or a fluorescence compound.

9. The organic electroluminescence device according to claim 6, wherein the light emitting layer comprises the delayed fluorescence compound as a delayed fluorescence host material.

10. The organic electroluminescence device according to claim 6, wherein the light emitting layer comprises the delayed fluorescence compound as a delayed fluorescence dopant material.

11. The organic electroluminescence device according to claim 6, wherein the light emitting layer comprising a second fluorescence dopant material.

12. The organic electroluminescence device according to claim 6, wherein the light emitting layer comprises a second fluorescence host material.

13. The organic electroluminescence device according to claim 6, wherein the light emitting layer comprises a delayed fluorescence compound as a phosphorescent host material.

14. The organic electroluminescence device according to claim 6, wherein the one or more organic thin film layers comprises the delayed fluorescence compound as a hole blocking material.

15. The organic electroluminescence device according to claim 6, wherein the one or more organic thin film layers comprises the delayed fluorescence compound as an electron transporting layer (ETL) material.

16. The organic electroluminescence device according to claim 6, wherein the device is an organic light emitting device.

17. The organic electroluminescent device according to claim 6, wherein the device is a lighting panel.

18. The organic electroluminescent device according to claim 6, wherein the device is a backlight panel.

* * * * *